(12) United States Patent
Heer et al.

(10) Patent No.: US 8,697,703 B2
(45) Date of Patent: Apr. 15, 2014

(54) PIPERAZINE DERIVATIVES FOR BLOCKING $Ca_v2.2$ CALCIUM CHANNELS

(75) Inventors: Jag Paul Heer, Cambridge (GB); Andrew Peter Cridland, Cambridge (GB); David Norton, Cambridge (GB)

(73) Assignee: Convergence Pharmaceuticals Limited, London (GB)

( * ) Notice: Subject to any disclaimer, the term of this patent is extended or adjusted under 35 U.S.C. 154(b) by 0 days.

(21) Appl. No.: 13/521,680

(22) PCT Filed: Jan. 14, 2011

(86) PCT No.: PCT/GB2011/050050
§ 371 (c)(1),
(2), (4) Date: Nov. 29, 2012

(87) PCT Pub. No.: WO2011/086377
PCT Pub. Date: Jul. 21, 2011

(65) Prior Publication Data
US 2013/0072499 A1 Mar. 21, 2013

(30) Foreign Application Priority Data
Jan. 15, 2010 (GB) .................................. 1000685.6

(51) Int. Cl.
*A61K 31/495* (2006.01)
(52) U.S. Cl.
USPC ................................. 514/253.05; 514/253.06
(58) Field of Classification Search
USPC ......................... 514/253.05, 253.06; 544/363
See application file for complete search history.

(56) References Cited

FOREIGN PATENT DOCUMENTS

| WO | WO-2007/072093 A1 | 6/2007 |
| WO | WO-2007/101007 A2 | 9/2007 |
| WO | WO-2008/011072 A2 | 1/2008 |
| WO | WO-2010/007072 A1 | 1/2010 |
| WO | WO-2010/007074 A1 | 1/2010 |
| WO | WO-2010/102633 A1 | 9/2010 |

OTHER PUBLICATIONS

Chemical Abstract Service, Columbus, Ohio.*
Rashbaum, R.F. "Treatment Options for Neuropathic Pain." Spine-Health. Available at: < http://www.spine-health.com/treatment/pain-management/treatment-options-neuropathic-pain >. Updated 2013.*
American Chemical Society (ACS). STN CAS Registry Database.*
Chemical Abstracts Service, Columbus, Ohio, US; Apr. 11, 2008, XP002624946, Database accession No. 1013729-85-5.
Chemical Abstracts Service, Columbus, Ohio, US; Apr. 11, 2008, XP002624947, Database accession No. 1013727-16-6.
Chemical Abstracts Service, Columbus, Ohio, US; Apr. 28, 2005, XP002624959, Database accession No. 849454-83-7.
Chemical Abstracts Service, Columbus, Ohio, US; Apr. 29, 2005, XP002624957, Database accession No. 849482-82-2.
Chemical Abstracts Service, Columbus, Ohio, US; Apr. 29, 2005, XP002624958, Database accession No. 849477-01-6.
Chemical Abstracts Service, Columbus, Ohio, US; Apr. 9, 2008, XP002624948, Database accession No. 1013017-84-9.
Chemical Abstracts Service, Columbus, Ohio, US; Dec. 10, 2004, XP002624960, Database accession No. 796096-78-1.
Chemical Abstracts Service, Columbus, Ohio, US; Feb. 12, 2008, XP002624950, Database accession No. 1002953-38-9.
Chemical Abstracts Service, Columbus, Ohio, US; Feb. 2, 2009, XP002624939, Database accession No. 1099809-63-8.
Chemical Abstracts Service, Columbus, Ohio, US; Feb. 2, 2009, XP002624940, Database accession No. 1099311-05-03.
Chemical Abstracts Service, Columbus, Ohio, US; Jan. 26, 2009, XP002624943, Database accession No. 10958844-13-5.
Chemical Abstracts Service, Columbus, Ohio, US; Jan. 26, 2009, XP002624944, Database accession No. 1095814-98-4.
Chemical Abstracts Service, Columbus, Ohio, US; Jan. 29, 2009, XP002624941, Database accession No. 1097529-89-9.
Chemical Abstracts Service, Columbus, Ohio, US; Jan. 29, 2009, XP002624942, Database accession No. 1097518-28-9.
Chemical Abstracts Service, Columbus, Ohio, US; Mar. 13, 2008, XP002624949, Database accession No. 1007729-33-0.
Chemical Abstracts Service, Columbus, Ohio, US; Mar. 28, 2006, XP002624952, Database accession No. 878248-96-5.
Chemical Abstracts Service, Columbus, Ohio, US; May 10, 2005, XP002624953, Database accession No. 850183-01-6.
Chemical Abstracts Service, Columbus, Ohio, US; May 10, 2005, XP002624954, Database accession No. 850150-92-4.
Chemical Abstracts Service, Columbus, Ohio, US; May 2, 2005, XP002624956, Database accession No. 849608-56-6.
Chemical Abstracts Service, Columbus, Ohio, US; May 3, 2005, XP002624955, Database accession No. 849679-21-6.
Chemical Abstracts Service, Columbus, Ohio, US; Oct. 29, 2009, XP002624934, Database accession No. 1190530-71-2.
Chemical Abstracts Service, Columbus, Ohio, US; Oct. 5, 2007, XP002624951, Database accession No. 949369-33-9.
Chemical Abstracts Service, Columbus, Ohio, US; Sep. 11, 2009, XP002624935, Database accession No. 1182569-32-9.

(Continued)

*Primary Examiner* — Andrew D Kosar
*Assistant Examiner* — John S Kenyon
(74) *Attorney, Agent, or Firm* — Foley & Lardner LLP

(57) ABSTRACT

The present invention relates to novel piperazine compounds; to pharmaceutical compositions containing the compounds; and to the use of the compounds in therapy to treat diseases for which blocking the $Ca_v2.2$ calcium channels is beneficial and to treat diseases for which blocking the $Ca_v2.2$ and $Ca_v3.2$ calcium channels is beneficial, e.g. to treat pain.

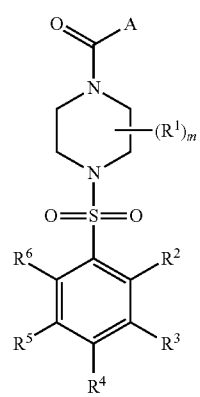

(I)

12 Claims, No Drawings

(56) References Cited

OTHER PUBLICATIONS

Chemical Abstracts Service, Columbus, Ohio, US; Sep. 17, 2004, XP002624962, Database accession No. 746617-64-1.
Chemical Abstracts Service, Columbus, Ohio, US; Sep. 21, 2008, XP002624945, Database accession No. 1050858-92-8.
Chemical Abstracts Service, Columbus, Ohio, US; Sep. 24, 2004, XP002624961, Database accession No. 750627-61-3.
Chemical Abstracts Service, Columbus, Ohio, US; Sep. 4, 2009, XP002624937, Database accession No. 1180395-43-0.
Chemical Abstracts Service, Columbus, Ohio, US; Sep. 4, 2009, XP002624938, Database accession No. 1180392-84-0.
Chemical Abstracts Service, Columbus, Ohio, US; Sep. 7, 2009, XP002624936, Database accession No. 1180988-76-4.
International Search Report and Written Opinion dated Apr. 4, 2011 in related PCT Application No. PCT/GB2011/050050.

* cited by examiner

PIPERAZINE DERIVATIVES FOR BLOCKING CA$_v$2.2 CALCIUM CHANNELS

FIELD OF THE INVENTION

The present invention relates to novel piperazine compounds; to processes for their preparation; to pharmaceutical compositions containing the compounds; and to the use of the compounds in therapy to treat diseases for which blocking the Ca$_v$2.2 calcium channels is beneficial and to treat diseases for which blocking the Ca$_v$2.2 and Ca$_v$3.2 calcium channels is beneficial, e.g. to treat pain.

BACKGROUND OF THE INVENTION

Pre-synaptic Ca$_v$2.2 (N-type) voltage-gated calcium channels in the dorsal horn of the spinal cord modulate the release of key pro-nociceptive neurotransmitters such as glutamate, substance P (SP) and calcitonin-gene-related peptide (CGRP), indicating the potential therapeutic use of Ca$_v$2.2 calcium channel blockers as analgesics.

Peptidic ω-conotoxins, isolated from the venom of cone snails, have been shown to be selective for Ca$_v$2.2 calcium channels and can block SP release in the spinal cord (Smith at al. (2002) Pain, 96: 119-127). Moreover, they have been shown to be antinociceptive in animal models of chronic pain following intrathecal administration (Bowersox at al. (1996) Journal of Pharmacology and Experimental Therapeutics, 279: 1243-1249; Smith et al. (2002) supra), and have been shown to be effective analgesics in clinical use, particularly in the treatment of neuropathic pain (Brose et al. (1997) Clinical Journal of Pain, 13: 256-259).

Winquist et al. has shown that Ca$_v$2.2 channels may offer the potential to reduce neuronal signalling, thereby treating disorders such as pain. However, side effect issues may impact the success of such an approach (Winquist et al. (2005) Biochemical Pharmacology, 70: 489-499). A number of journal articles have been published on the effect of natural inhibitors of Ca$_v$2.2 channels (see Bowersox et al. (1996) Journal of Pharmacology and Experimental Therapeutics 279 (3):1243-1249; Scott et al. (2002) European Journal of Pharmacology 451(3):279-286). In addition, several journal articles have been published on the phenotypic characterisation of transgenic mice lacking the Ca$_v$2.2 gene (see Saegusa et al. (2001) EMBO J. 20(10):2349-2356; Kim et al. (2001) Mol. Cell. Neurosci. 18(2):235-245). These articles support the stance that tonic inhibition of Ca$_v$2.2 may result in cardiovascular (hypotension) and CNS (sedation) side effects at therapeutic concentrations.

Due to these drawbacks of tonic Ca$_v$2.2 inhibitors, it is the object of the invention to provide an alternative class of Ca$_v$2.2 antagonist: a state- or use-dependent Cav2.2 blocker, which has the potential to selectively inhibit highly active channels contributing to the pathophysiology of chronic pain whilst sparing the contributions of Cav2.2 to wider physiological levels of activity within the peripheral and central nervous system. Therefore, one object of the invention is to identify novel compounds for use in therapy that block Ca$_v$2.2 calcium channels under conditions of increased neuronal excitability, so-called use-dependent blockers, as is the case in chronic pain syndromes.

Recent studies also provide evidence for a contribution of T-type calcium channels to the pathophysiology of acute (nociceptive) and chronic pain. T-type channels exist as three distinct subtypes, namely Ca$_v$3.1-3.3, which differ in their expression and functional properties. All three subtypes are expressed in DRG neurones where their knockdown with anti-sense approaches has highlighted the role in particular of Ca$_v$3.2 to chronic pain (Bourinet et al (2005) EMBO J. 24:315-24). Further studies have indicated that these channels are functionally up-regulated in the rat streptozotocin model of diabetic neuropathy (Messinger et al (2009) Pain. 145:184-95) and in genetically obesity prone Ob/Ob mice (Latham et al (2009) Diabetes 58:2656-65) where they contribute to the measured hyperalgesia. Consequently, T-type calcium channel (Ca$_v$3.2) inhibitors may have therapeutic applications in the treatment of pain. Furthermore, as already discussed for the N-type calcium channels (Ca$_v$2.2), inhibitors which possess a use-dependent mechanism of action may be expected to show an optimum balance between efficacy and side effects. Thus, specifically targeting both N- and T-calcium channel types with the same inhibitor acting as a use-dependent antagonist has the potential to simultaneously inhibit multiple points of the signalling pathway which contribute to the conscious perception of pain. This has the potential to deliver additive or synergistic effects which may lead to increased efficacy as manifested in a greater magnitude of response and/or a greater responder rate to treatment in a diverse population of patients with chronic pain syndromes. A therapeutic benefit may also be achieved with a better tolerability profile as a result of this improved efficacy.

Therefore, it is a further object of the invention to identify novel compounds for use in therapy that preferentially block Ca$_v$2.2 and Ca$_v$3.2 calcium channels under conditions of increased neuronal excitability, so-called use-dependent blockers, as is the case in chronic pain syndromes.

WO 2008/024284 (Merck & Co) describes a series of sulfonylated piperazines as cannabinoid-1 (CB1) receptor modulators which are claimed to be useful in the treatment for example of psychosis, cognitive disorders and Alzheimer's disease. WO 96/31501 (Schering Corporation) describes carbonyl-piperazinyl and piperidinyl compounds which inhibit farnesyl protein transferase. WO 2005/113542 (Elan Pharmaceuticals) describes N-cyclic sulfonamido compounds which inhibit gamma secretase and beta-amyloid peptide release and/or its synthesis.

SUMMARY OF THE INVENTION

In a first aspect, there is provided a compound of formula (I), or a salt thereof:

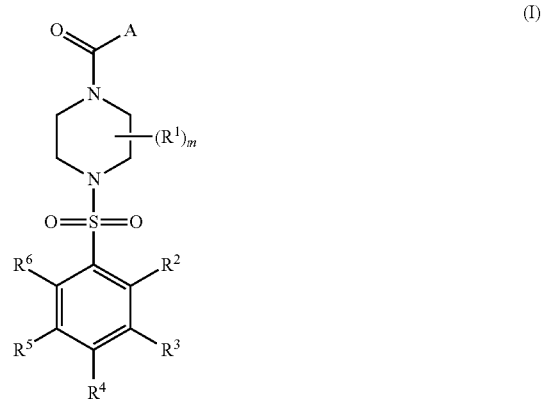

wherein A is selected from
(a) 2-quinolinyl,
(b) 5-quinolinyl,
(c) 7-quinolinyl, (d) 8-quinolinyl, and
(e) isoquinolinyl;
and wherein A is unsubstituted or substituted with 1 to 3 substituents independently selected from $C_{1-4}$ alkyl;
m is 0, 1 or 2;
where present, each $R^1$ is $C_{1-4}$ alkyl;
$R^2$ is H, halogen, $C_{1-4}$ alkyl, $C_{1-4}$ alkoxy, cyano, $C_{1-4}$ haloalkyl or $C_{1-4}$ haloalkoxy;
$R^3$ is H, halogen, $C_{1-4}$ alkyl, $C_{1-4}$ alkoxy, cyano, $C_{1-4}$ haloalkyl or $C_{1-4}$ haloalkoxy;
$R^4$ is H, halogen, $C_{1-4}$ alkyl, $C_{1-4}$ alkoxy, cyano, $C_{1-4}$ haloalkyl or $C_{1-4}$ haloalkoxy;
$R^5$ is H, halogen, $C_{1-4}$ alkyl, $C_{1-4}$ alkoxy, cyano, $C_{1-4}$ haloalkyl or $C_{1-4}$ haloalkoxy;
$R^6$ is H, halogen, $C_{1-4}$ alkyl, $C_{1-4}$ alkoxy, cyano, $C_{1-4}$ haloalkyl or $C_{1-4}$ haloalkoxy; such that at least 1 of $R^2$, $R^3$, $R^4$, $R^5$ and $R^6$ is a group other than H;
with the proviso that the compound is not 8-({4-[(3-bromophenyl)sulfonyl]-1-piperazinyl}carbonyl)quinoline, 8-({4-[(4-fluorophenyl)sulfonyl]-1-piperazinyl}carbonyl)quinoline, 8-{[4-({4-[(trifluoromethyl)oxy]phenyl}sulfonyl)-1-piperazinyl]carbonyl}quinoline, 8-[(4-{[4-(trifluoromethyl)phenyl]sulfonyl}-1-piperazinyl)carbonyl]quinoline, 2-{[4-([(trifluoromethyl)oxy]phenyl}sulfonyl)-1-piperazinyl]carbonyl}quinoline, 8-({4-[(4-bromophenyl)sulfonyl]-1-piperazinyl}carbonyl)quinoline, 2-({4-[(4-bromophenyl)sulfonyl]-1-piperazinyl}carbonyl)quinoline, 8-[(4-{[4-chloro-3-(trifluoromethyl)phenyl]sulfonyl}-1-piperazinyl)carbonyl]quinoline, 4-{[4-(8-quinolinylcarbonyl)-1-piperazinyl]sulfonyl}benzonitrile, 2-[(4-{[4-(trifluoromethyl)phenyl]sulfonyl}-1-piperazinyl)carbonyl]quinoline, 2-[(4-{[3-(trifluoromethyl)phenyl]sulfonyl}-1-piperazinyl)carbonyl]quinoline, 2-({4-[(3-chlorophenyl)sulfonyl]-1-piperazinyl}carbonyl)quinoline, 2-({4-[(4-fluorophenyl)sulfonyl]-1-piperazinyl}carbonyl)quinoline, or 2-({4-[(3-fluorophenyl)sulfonyl]-1-piperazinyl}carbonyl)quinoline.

In a second aspect, there is provided a compound of formula (I), or a pharmaceutically acceptable salt thereof, for use in therapy:

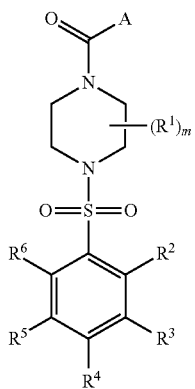

wherein A is selected from
(a) 2-quinolinyl,
(b) 5-quinolinyl,
(c) 7-quinolinyl,
(d) 8-quinolinyl, and
(e) isoquinolinyl;
and wherein A is unsubstituted or substituted with 1 to 3 substituents independently selected from $C_{1-4}$ alkyl;
m is 0, 1 or 2;
where present, each $R^1$ is $C_{1-4}$ alkyl;
$R^2$ is H, halogen, $C_{1-4}$ alkyl, $C_{1-4}$ alkoxy, cyano, $C_{1-4}$ haloalkyl or $C_{1-4}$ haloalkoxy;
$R^3$ is H, halogen, $C_{1-4}$ alkyl, $C_{1-4}$ alkoxy, cyano, $C_{1-4}$ haloalkyl or $C_{1-4}$ haloalkoxy;
$R^4$ is H, halogen, $C_{1-4}$ alkyl, $C_{1-4}$ alkoxy, cyano, $C_{1-4}$ haloalkyl or $C_{1-4}$ haloalkoxy;
$R^5$ is H, halogen, $C_{1-4}$ alkyl, $C_{1-4}$ alkoxy, cyano, $C_{1-4}$ haloalkyl or $C_{1-4}$ haloalkoxy;
$R^6$ is H, halogen, $C_{1-4}$ alkyl, $C_{1-4}$ alkoxy, cyano, $C_{1-4}$ haloalkyl or $C_{1-4}$ haloalkoxy;
such that at least 1 of $R^2$, $R^3$, $R^4$, $R^5$ and $R^6$ is a group other than H.

According to a further aspect, there is provided the use of a compound as defined in the second aspect, or a pharmaceutically acceptable salt thereof, in the manufacture of a medicament for the treatment or prophylaxis of pain.

According to a further aspect, there is provided a method for the treatment or prophylaxis of pain in a human or animal in need thereof comprising administering to said human or animal a therapeutically effective amount of a compound as defined in the second aspect, or a pharmaceutically acceptable salt thereof.

According to a further aspect, there is provided a pharmaceutical composition comprising (a) a compound as defined in the second aspect, or a pharmaceutically acceptable salt thereof, and (b) a pharmaceutically acceptable excipient.

DETAILED DESCRIPTION OF THE INVENTION

In a first aspect, there is provided a compound of formula (I), or a salt thereof:

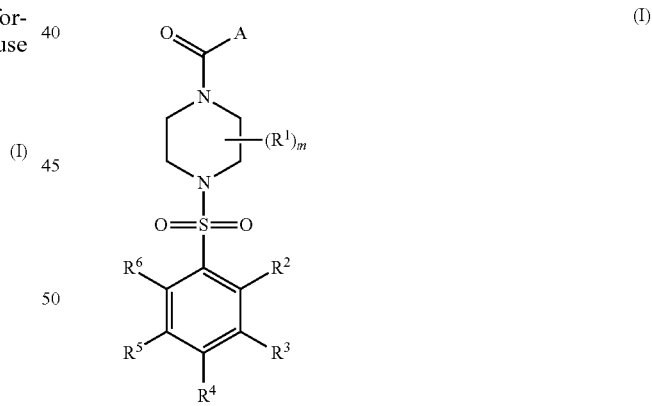

$R^3$ is H, halogen, $C_{1-4}$ alkyl, $C_{1-4}$ alkoxy, cyano, $C_{1-4}$ haloalkyl or $C_{1-4}$ haloalkoxy;
$R^4$ is H, halogen, $C_{1-4}$ alkyl, $C_{1-4}$ alkoxy, cyano, $C_{1-4}$ haloalkyl or $C_{1-4}$ haloalkoxy;
$R^5$ is H, halogen, $C_{1-4}$ alkyl, $C_{1-4}$ alkoxy, cyano, $C_{1-4}$ haloalkyl or $C_{1-4}$ haloalkoxy;
$R^6$ is H, halogen, $C_{1-4}$ alkyl, $C_{1-4}$ alkoxy, cyano, $C_{1-4}$ haloalkyl or $C_{1-4}$ haloalkoxy;
such that at least 1 of $R^2$, $R^3$, $R^4$, $R^5$ and $R^6$ is a group other than H;
with the proviso that the compound is not 8-({4-[(3-bromophenyl)sulfonyl]-1-piperazinyl}carbonyl)quinoline, 8-({4-[(4-fluorophenyl)sulfonyl]-1-piperazinyl}carbonyl)quinoline, 8-{[4-({4-[(trifluoromethyl)oxy]phenyl}sulfonyl)-1-piperazinyl]carbonyl}quinoline, 8-[(4-{[4-(trifluoromethyl)phenyl]sulfonyl}-1-piperazinyl)carbonyl]quinoline, 2-{[4-({4-[(trifluoromethyl)oxy]phenyl}sulfonyl)-1-piperazinyl]carbonyl}quinoline, 8-({4-[(4-bromophenyl)sulfonyl}-1-piperazinyl]carbonyl)quinoline, 2-({4-[(4-bromophenyl)sulfonyl]-1-piperazinyl}carbonyl)quinoline, 8-[(4-{[4-chloro-3-(trifluoromethyl)phenyl]sulfonyl}-1-piperazinyl)carbonyl]quinoline, 4-{[4-(8-quinolinylcarbonyl)-1-piperazinyl]sulfonyl}benzonitrile, 2-[(4-{(4-(trifluoromethyl)phenyl]sulfonyl}-1-piperazinyl)carbonyl]quinoline, 2-[(4-{[3-(trifluoromethyl)phenyl]sulfonyl}-1-piperazinyl)carbonyl]quinoline, 2-({4-[(3-chlorophenyl)sulfonyl]-1-piperazinyl}carbonyl)quinoline, 2-({4-[(4-fluorophenyl)sulfonyl]-1-piperazinyl}carbonyl)quinoline, or 2-({4-[(3-fluorophenyl)sulfonyl]-1-piperazinyl}carbonyl)quinoline.

In a second aspect, there is provided a compound of formula (I), or a pharmaceutically acceptable salt thereof, for use in therapy:

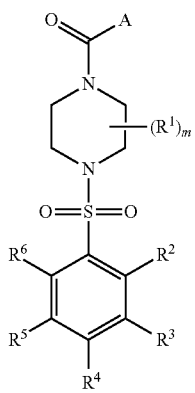

(I)

wherein A is selected from
(a) 2-quinolinyl,
(b) 5-quinolinyl,
(c) 7-quinolinyl,
(d) 8-quinolinyl, and
(e) isoquinolinyl;
and wherein A is unsubstituted or substituted with 1 to 3 substituents independently selected from $C_{1-4}$ alkyl;
m is 0, 1 or 2;
where present, each $R^1$ is $C_{1-4}$ alkyl;
$R^2$ is H, halogen, $C_{1-4}$ alkyl, $C_{1-4}$ alkoxy, cyano, $C_{1-4}$ haloalkyl or $C_{1-4}$ haloalkoxy;
$R^3$ is H, halogen, $C_{1-4}$ alkyl, $C_{1-4}$ alkoxy, cyano, $C_{1-4}$ haloalkyl or $C_{1-4}$ haloalkoxy;
$R^4$ is H, halogen, $C_{1-4}$ alkyl, $C_{1-4}$ alkoxy, cyano, $C_{1-4}$ haloalkyl or $C_{1-4}$ haloalkoxy;
$R^5$ is H, halogen, $C_{1-4}$ alkyl, $C_{1-4}$ alkoxy, cyano, $C_{1-4}$ haloalkyl or $C_{1-4}$ haloalkoxy;
$R^6$ is H, halogen, $C_{1-4}$ alkyl, $C_{1-4}$ alkoxy, cyano, $C_{1-4}$ haloalkyl or $C_{1-4}$ haloalkoxy;
such that at least 1 of $R^2$, $R^3$, $R^4$, $R^5$ and $R^6$ is a group other than H.

It will be appreciated that in compounds of formula (I), where present, each $R^1$ may be attached to any one of the possible four carbon atoms of the piperazine group.

The term '$C_{1-4}$alkyl' as used herein as a group or a part of a group refers to a linear or branched saturated hydrocarbon group containing from 1 to 4 carbon atoms. Examples of $C_{1-4}$ alkyl include methyl, ethyl, n-propyl and isopropyl. Unless a particular structure is specified, the term propyl includes all straight and branched chain forms e.g. propyl includes n-propyl and isopropyl.

As used herein, the term '$C_{1-4}$ alkoxy' (when used as a group or as part of a group) refers to an —O—$C_{1-4}$ alkyl group wherein $C_{1-4}$ alkyl is as defined hereinbefore.

The term 'halogen' as used herein refers to fluoro, chloro, bromo or iodo.

The term '$C_{1-4}$ haloalkyl' as used herein refers to a $C_{1-4}$ alkyl group as defined herein substituted with one or more halogen groups, e.g. $CF_3$, $CF_2H$ or $CF_3CH_2$.

The term '$C_{1-4}$ haloalkoxy' as used herein refers to an $C_{1-4}$ alkoxy group as defined herein substituted with one or more halogen groups, e.g. —O—$CF_3$.

In one embodiment of the first or second aspect, A is unsubstituted or substituted with 1 to 3 methyl groups.

In one embodiment of the first or second aspect, m is 0 or 1. In a further embodiment, m is 0.

In one embodiment of the first or second aspect, $R^1$ is methyl.

In one embodiment of the first or second aspect, $R^2$ is H or methyl.

In one embodiment of the first or second aspect, $R^3$ is H.

In one embodiment of the first or second aspect, $R^4$ is cyano, $C_{1-4}$ haloalkyl or $C_{1-4}$ haloalkoxy. In a further embodiment, $R^4$ is cyano, trifluoromethyl or trifluoromethoxy.

In one embodiment of the first or second aspect, $R^5$ is H.

In one embodiment of the first or second aspect, $R^4$ is trifluoromethyl and $R^2$, $R^3$ and $R^5$ are H.

In one embodiment of the first or second aspect, $R^4$ is trifluoromethoxy and $R^2$, $R^3$ and $R^5$ are H.

In one embodiment of the first or second aspect, $R^4$ is cyano and $R^2$, $R^3$ and $R^5$ are H.

In one embodiment of the first or second aspect, $R^4$ is cyano, $R^2$ is methyl and $R^3$ and $R^5$ are H.

In one embodiment of the first or second aspect, A is selected from 2-quinolinyl and 7-quinolinyl. In a further embodiment, A is selected from 7-quinolinyl.

In one embodiment of the first or second aspect, A is isoquinolinyl. In a further embodiment, A is selected from 1-isoquinolinyl, 3-isoquinolinyl, 4-isoquinolinyl, 5-isoquinolinyl, 6-isoquinolinyl and 8-isoquinolinyl. In a still further embodiment, A is selected from 3-isoquinolinyl, 4-isoquinolinyl and 8-isoquinolinyl.

In one embodiment of the first or second aspect, A is selected from 2-quinolinyl and 7-quinolinyl, wherein A is unsubstituted or substituted with 1 to 3 methyl groups; m is 0 or 1; where present, $R^1$ is methyl; $R^2$ is H or methyl; $R^3$ is H; $R^4$ is cyano, $C_{1-4}$ haloalkyl or $C_{1-4}$ haloalkoxy (in particular $R^4$ is cyano, trifluoromethyl or trifluoromethoxy); $R^5$ is H.

In one embodiment of the first or second aspect, A is isoquinolinyl (in particular 1-isoquinolinyl, 3-isoquinolinyl, 4-isoquinolinyl, 5-isoquinolinyl, 6-isoquinolinyl and 8-isoquinolinyl, more particularly 3-isoquinolinyl, 4-isoquinolinyl and 8-isoquinolinyl), wherein A is unsubstituted or substituted with 1 to 3 methyl groups; m is 0 or 1; where present, $R^1$ is methyl; $R^2$ is H or methyl; $R^3$ is H; $R^4$ is cyano, $C_{1-4}$ haloalkyl or $C_{1-4}$ haloalkoxy (in particular $R^4$ is cyano, trifluoromethyl or trifluoromethoxy); $R^5$ is H.

In one embodiment of the first or second aspect, the compound or salt is selected from the exemplified Compounds 1 to 47, or a salt thereof.

In a further embodiment of the first or second aspect, the compound or salt is selected from the exemplified Compounds 1 to 31, or a salt thereof.

In one embodiment of the second aspect, the compound or salt is selected from
- 7-[(((2S)-2-methyl-4-{[4-(trifluoromethyl)phenyl]sulfonyl}-1-piperazinyl)carbonyl]quinoline;
- 8-methyl-7-{[4-({4-[(trifluoromethyl)oxy]phenyl}sulfonyl)-1-piperazinyl]carbonyl}quinoline;
- 8-{[4-({4-[(trifluoromethyl)oxy]phenyl}sulfonyl)-1-piperazinyl]carbonyl}quinoline;
- 2-[(4-{[4-(trifluoromethyl)phenyl]sulfonyl}-1-piperazinyl)carbonyl]quinoline;
- 7-[(4-{[4-(trifluoromethyl)phenyl]sulfonyl}-1-piperazinyl)carbonyl]quinoline;
- 8-[(4-{[4-(trifluoromethyl)phenyl]sulfonyl}-1-piperazinyl)carbonyl]quinoline;
- 5-[(4-{[4-(trifluoromethyl)phenyl]sulfonyl}-1-piperazinyl)carbonyl]quinoline;
- 4-{(3S)-3-methyl-4-(7-quinolinylcarbonyl)-1-piperazinyl]sulfonyl}benzonitrile;
- 3-methyl-4-{[4-(7-quinolinylcarbonyl)-1-piperazinyl]sulfonyl}benzonitrile;
- 3-methyl-4-{(3S)-3-methyl-4-(7-quinolinylcarbonyl)-1-piperazinyl]sulfonyl}benzonitrile;
- 3-methyl-4-({4-[(2-methyl-7-quinolinyl)carbonyl]-1-piperazinyl}sulfonyl)benzonitrile;
- 3-methyl-4-({(3S)-3-methyl-4-[(2-methyl-7-quinolinyl)carbonyl]-1-piperazinyl}sulfonyl)benzonitrile;
- 3-methyl-4-({(3S)-3-methyl-4-(8-quinolinylcarbonyl)-1-piperazinyl}sulfonyl)benzonitrile;
- 3-methyl-4-{(3S)-3-methyl-4-(5-quinolinylcarbonyl)-1-piperazinyl]sulfonyl}benzonitrile;
- 8-methyl-7-[(4-{[4-(trifluoromethyl)phenyl]sulfonyl}-1-piperazinyl)carbonyl]quinoline
- 4-({(3S)-3-methyl-4-[(8-methyl-7-quinolinyl)carbonyl]-1-piperazinyl}sulfonyl)benzonitrile;
- 3-methyl-4-({(3S)-3-methyl-4-[(8-methyl-7-quinolinyl)carbonyl]-1-piperazinyl}sulfonyl)benzonitrile;
- 7-{[4-({4-[(trifluoromethyl)oxy]phenyl}sulfonyl)-1-piperazinyl]carbonyl}quinoline;
- 7-{[(2S)-2-methyl-4-({4-[(trifluoromethyl)oxy]phenyl}sulfonyl)-1-piperazinyl]carbonyl}quinoline;
- 7-{[(2S)-4-({4-[(difluoromethyl)oxy]phenyl}sulfonyl)-2-methyl-1-piperazinyl]carbonyl}quinoline; and
- 7-{[(2S)-4-({4-[(difluoromethyl)oxy]phenyl}sulfonyl)-2-methyl-1-piperazinyl]carbonyl}-8-methylquinoline; or a salt of any of the compounds.

In one embodiment of the first or second aspect, the compound or salt is selected from
- 8-[((2S)-2-methyl-4-{[4-(trifluoromethyl)phenyl]sulfonyl}-1-piperazinyl)carbonyl]isoquinoline;
- 1-(4-{[4-(trifluoromethyl)phenyl]sulfonyl}-1-piperazinyl]carbonyl]isoquinoline;
- 5-[(4-{[4-(trifluoromethyl)phenyl]sulfonyl}-1-piperazinyl)carbonyl]isoquinoline;
- 3-[(4-{[4-(trifluoromethyl)phenyl]sulfonyl}-1-piperazinyl)carbonyl]isoquinoline;
- 8-[(4-([4-(trifluoromethyl)phenyl]sulfonyl}-1-piperazinyl)carbonyl]isoquinoline;
- 4-[(4-{[4-(trifluoromethyl)phenyl]sulfonyl}-1-piperazinyl)carbonyl]isoquinoline;
- 4-{[4-(8-isoquinolinylcarbonyl)-1-piperazinyl]sulfonyl}-3-methylbenzonitrile;
- 4-{[(3S)-4-(8-isoquinolinylcarbonyl)-3-methyl-1-piperazinyl]sulfonyl}benzonitrile;
- 4-{[(3S)-4-(6-isoquinolinylcarbonyl)-3-methyl-1-piperazinyl]sulfonyl}benzonitrile; and
- 4-{[(3S)-4-(8-isoquinolinylcarbonyl)-3-methyl-1-piperazinyl]sulfonyl}-3-methylbenzonitrile; or a salt of any of the compounds.

In one embodiment of the first aspect, the compound or salt as defined is selected from
- 7-[((2S)-2-methyl-4-{[4-(trifluoromethyl)phenyl]sulfonyl}-1-piperazinyl)carbonyl]quinoline;
- 8-{[4-({4-(trifluoromethyl)oxy]phenyl}sulfonyl)-1-piperazinyl]carbonyl}quinoline;
- 2-[(4-{[4-(trifluoromethyl)phenyl]sulfonyl}-1-piperazinyl)carbonyl]quinoline;
- 7-[(4-{[4-(trifluoromethyl)phenyl]sulfonyl}-1-piperazinyl)carbonyl]quinoline;
- 5-[(4-{[4-(trifluoromethyl)phenyl]sulfonyl}-1-piperazinyl)carbonyl]quinoline;
- 4-{[(3S)-3-methyl-4-(7-quinolinylcarbonyl)-1-piperazinyl]sulfonyl}benzonitrile;
- 3-methyl-4-{[4-(7-quinolinylcarbonyl)-1-piperazinyl]sulfonyl}benzonitrile;
- 3-methyl-4-{[(3S)-3-methyl-4-(7-quinolinylcarbonyl)-1-piperazinyl]sulfonyl}benzonitrile;
- 3-methyl-4-({4-[(2-methyl-7-quinolinyl)carbonyl]-1-piperazinyl}sulfonyl)benzonitrile;
- 3-methyl-4-({(3S)-3-methyl-4-[(2-methyl-7-quinolinyl)carbonyl]-1-piperazinyl}sulfonyl)benzonitrile;
- 3-methyl-4-{[(3S)-3-methyl-4-(8-quinolinylcarbonyl)-1-piperazinyl]sulfonyl}benzonitrile;
- 3-methyl-4-{[(3S)-3-methyl-4-(5-quinolinylcarbonyl)-1-piperazinyl]sulfonyl}benzonitrile;
- 8-methyl-7-[(4-{[4-(trifluoromethyl)phenyl]sulfonyl}-1-piperazinyl)carbonyl]quinoline
- 4-({(3S)-3-methyl-4-[(8-methyl-7-quinolinyl)carbonyl]-1-piperazinyl}sulfonyl)benzonitrile;
- 3-methyl-4-({(3S)-3-methyl-4-[(8-methyl-7-quinolinyl)carbonyl]-1-piperazinyl}sulfonyl)benzonitrile;
- 7-{[4-({4-[(trifluoromethyl)oxy]phenyl}sulfonyl)-1-piperazinyl]carbonyl}quinoline;
- 7-{[(2S)-2-methyl-4-({4-[(trifluoromethyl)oxy]phenyl}sulfonyl)-1-piperazinyl]carbonyl}quinoline;
- 7-{[(2S)-4-({4-[(difluoromethyl)oxy]phenyl}sulfonyl)-2-methyl-1-piperazinyl]carbonyl}quinoline; and
- 7-{[(2S)-4-({4-[(difluoromethyl)oxy]phenyl}sulfonyl)-2-methyl-1-piperazinyl]carbonyl}-8-methylquinoline; or a salt of any of the compounds.

Certain compounds as defined in the first or second aspect may in some circumstances form acid addition salts thereof. It will be appreciated that for use in medicine compounds as defined in the first or second aspect may be used as salts, in which case the salts should be pharmaceutically acceptable. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

It will be appreciated by those skilled in the art that certain protected derivatives of the compounds as defined in the first or second aspect, which may be made prior to a final deprotection stage, may not possess pharmacological activity as such, but may, in certain instances, be administered orally or parenterally and thereafter metabolised in the body to form compounds as defined in the first or second aspect which are pharmacologically active. Such derivatives may therefore be described as "prodrugs". All protected derivatives and prodrugs of compounds defined in the first or second aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds as defined in the first or second aspect. Therefore, in a further aspect, the invention provides a prodrug of a compound as defined in the first or second aspect.

It will be appreciated that certain compounds as defined in the first or second aspect, or their salts, may exist as solvates, such as hydrates. Where solvates exist, this invention includes within its scope stoichiometric and non-stoichiometric solvates.

It will be appreciated that certain compounds as defined in the first or second aspect, or their salts, may exist in more than one polymorphic form. The invention extends to all such forms whether in a pure polymorphic form or when admixed with any other material, such as another polymorphic form.

It will appreciated that certain compounds as defined in the first or second aspect, or their salts, may exist as tautomers. The invention also extends to any tautomeric forms and mixtures thereof.

Certain compounds as defined in the first or second aspect are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis.

The subject invention also includes isotopically-labelled compounds, which are identical to the compounds as defined in the first or second aspect, but for the fact that one or more atoms are replaced by an atom having an atomic mass or mass number different from the atomic mass or mass number most commonly found in nature. Examples of isotopes that can be incorporated into compounds of the invention include isotopes of H, carbon, nitrogen, fluorine, such as $^3$H, $^{11}$C, $^{14}$C and $^{18}$F.

Compounds as defined in the first or second aspect and salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds as defined in the first or second aspect and following of this invention can generally be prepared by carrying out the procedures disclosed in the Schemes and/or in the Examples below, by substituting a readily available isotopically labelled reagent for a non-isotopically labelled reagent. In one embodiment, compounds as defined in the first or second aspect or salts thereof are not isotopically labelled.

Throughout the specification, general formulae are designated by Roman numerals (I), (II), (III), (IV), etc. Subsets of these general formulae are defined as (Ia), (Ib), (Ic), etc. . . . (IVa), (IVb), (IVc), etc.

Compounds as defined in the first or second aspect may be prepared as set forth in the following Schemes and in the supporting compounds. The following processes form further aspects of the invention.

The present invention also provides a process for the preparation of a compound as defined in the first or second aspect, or a salt thereof, which process comprises:

(a) reacting a compound of formula (II)

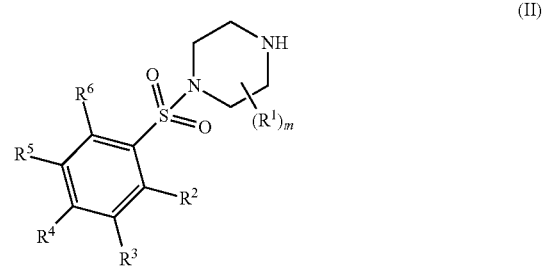

or a derivative thereof, with a compound of formula (III)

wherein $R^1$, $R^2$, $R^3$, $R^4$, $R^5$, $R^6$, A and m are as defined in the first or second aspect and L' represents a suitable leaving group such as a halogen atom (e.g. chlorine or bromine) or a hydroxyl group activated by commercially available amide coupling reagents (for example, HOBT, HBTU or HATU); or (b) interconversion to other compounds as defined in the first or second aspect.

Process (a) typically comprises reaction of a compound of formula (II) with a compound of formula (III) in a suitable solvent such as acetonitrile, tetrahydrofuran, N,N-dimethylformamide or dichloromethane, in the presence of a suitable base, (for example, triethylamine, di-isopropylethylamine or DIPEA) at 0° C. to ambient temperature (for example, room temperature).

Process (b) may be performed using conventional interconversion procedures such as epimerisation, oxidation, reduction, alkylation, nucleophilic or electrophilic aromatic substitution. One such example of interconversion may be interconversion of a compound as defined in the first or second aspect wherein $R^4$ represents bromine to a compound as defined in the first or second aspect wherein $R^4$ represents cyano. Such interconversion may be carried out by treating the bromine compound with a cyanide salt (for example copper (I) cyanide) in a suitable solvent (such as N,N-dimethylformamide) at elevated temperatures (such as 200° C. using microwave irradiation). Alternatively the interconversion may be carried out using a cyanide salt (for example zinc cyanide) in the presence of a source of a palladium catalyst (for example tris(dibenzylideneacetone)dipalladium(0) and ligand (for example 1, 1'-bis(diphenylphosphino)ferrocene) in a suitable solvent (such as N,N-dimethylformamide) at elevated temperatures (such as 120° C.).

This kind of interconversion may also be carried out on intermediates of compounds as defined in the first or second aspect.

Compounds of formula (II) may be prepared in accordance with the following Scheme:

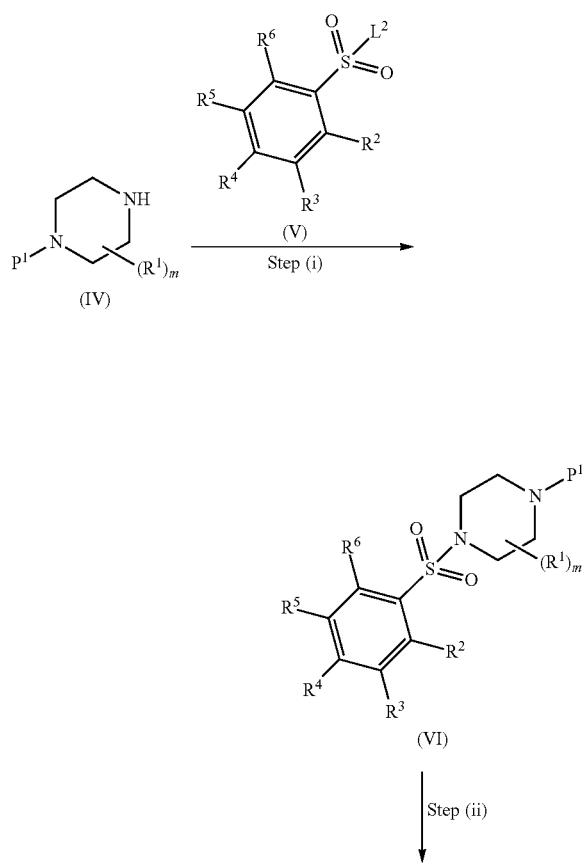

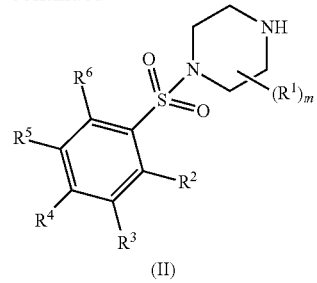

wherein $R^1$, $R^2$, $R^3$, $R^4$, $R^5$, $R^6$ and m are as defined in the first or second aspect, $L^2$ represents a suitable leaving group such as a halogen atom (e.g. chloro or bromo) and $P^1$ represents a suitable protecting group such as t-butoxycarbonyl (BOC). Alternatively, if $P^1$ is H then step (ii) is not required.

Step (i) typically comprises reacting a compound of formula (IV) and (V) in a suitable solvent, such as DCM or MeCN in the presence of a base (for example triethylamine, di-isopropylethylamine or DIPEA) at 0° C. to ambient temperature (for example ambient temperature). Alternatively, step (i) may typically be carried out using a suitable base as a solvent, for example pyridine, or step (i) may also be carried out in a solvent mixture of THF and water, using a suitable base such as sodium hydroxide.

Step (ii) typically comprises a deprotection reaction. For example, when $P^1$ represents t-butoxycarbonyl, step (ii) will typically comprise treatment with an acid, for example hydrochloric acid or trifluoroacetic acid, in a solvent (such as 1,4-dioxane, dichloromethane or a mixture of methanol and 1,4-dioxane).

Compounds of formula (IV) are either commercially available or may be prepared by known methods.

Compounds of formula (V) are either commercially available, or may be prepared by known methods. For example, they may be prepared according to the following Scheme:

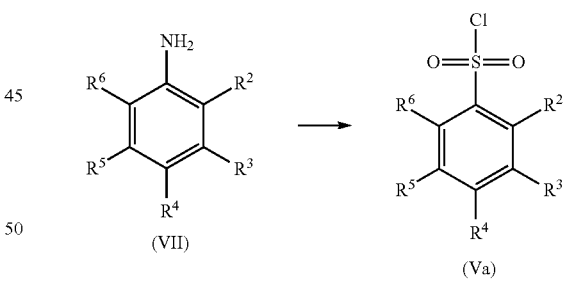

wherein $R^2$, $R^3$, $R^4$, $R^5$ and $R^6$ are as defined in the first or second aspect In the above reaction, compound (VII) is dissolved in acetic acid and concentrated sulphuric acid and the solution cooled to around 0° C. Sodium nitrite is then added and the reaction mixture kept cool before adding a saturated solution of sulphur dioxide in acetic acid to the reaction mixture while maintaining the temperature below 10° C.

Compounds of formula (VII) are either commercially available, or may be prepared by known methods.

Compounds of formula (III) are either commercially available or may be prepared by known methods. They may for example also be prepared in accordance with the following Scheme:

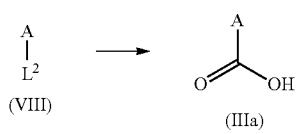

In the above reaction, a compound (VIII) is typically reacted with a suitable organolithium reagent, such as n-butyllithium, at a suitable temperature, for example at −78° C., in a suitable solvent, such as THF, followed by reaction with carbon dioxide at a suitable temperature such as at −78° C.

Compounds of formula (VIII) are either commercially available or may be prepared by known methods. One such known method is for example the reaction

This reaction is described in *J. Med. Chem.*, 2005, 48(15), 4972-4982.

The compounds as defined in the first or second aspect, or salts thereof, may be used to treat diseases for which blocking the $Ca_v2.2$ calcium channels is beneficial and to treat diseases for which blocking the $Ca_v2.2$ and $Ca_v3.2$ calcium channels is beneficial. Therefore, according to one aspect, the compounds as defined in the first or second aspect may be useful in the treatment or prophylaxis of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

'Chronic articular pain' conditions include rheumatoid arthritis, osteoarthritis, rheumatoid spondylitis, gouty arthritis and juvenile arthritis.

'Pain associated with functional bowel disorders' includes non-ulcer dyspepsia, non-cardiac chest pain and irritable bowel syndrome.

'Neuropathic pain' syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

'Inflammatory pain' conditions include skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastro esophageal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

Compounds as defined in the first or second aspect may also be useful in the treatment or prophylaxis of disorders treatable and/or preventable with anti-convulsive agents, such as epilepsy including post-traumatic epilepsy, obsessive compulsive disorders (OCD), bipolar disorders, sleep disorders (including circadian rhythm disorders, insomnia & narcolepsy), tics (e.g. Giles de la Tourette's syndrome), ataxias, muscular rigidity (spasticity), and temporomandibular joint dysfunction. "Epilepsy" is intended to include the following seizures: simple partial seizures, complex partial seizures, secondary generalised seizures, generalised seizures including absence seizures, myoclonic seizures, clonic seizures, tonic seizures, tonic clonic seizures and atonic seizures.

Another condition which may potentially be treated by compounds as defined in the first or second aspect is spasticity or muscular hypertonicity.

It is believed that compounds as defined in the first or second aspect are particularly useful in the treatment or prophylaxis of pain, more particularly neuropathic pain, inflammatory pain and migraine, and epilepsy.

Thus, in an embodiment of the second aspect, the therapy is to the treatment or prophylaxis of any of the disorders described herein, in particular pain. In one particular embodiment, the therapy is to the treatment of any of the disorders described herein, in particular pain.

According to a further aspect, there is provided a use of a compound as defined in the second aspect, or a pharmaceutically acceptable salt thereof, in the manufacture of a medicament for the treatment or prophylaxis of any of the disorders herein, in particular pain. More particularly, there is provided a use of a compound as defined in the second aspect, or a pharmaceutically acceptable salt thereof, in the manufacture of a medicament for the treatment of any of the disorders herein.

According to another aspect, there is provided a method of treatment or prophylaxis of any of the disorders herein, in particular pain in humans, which method comprises the administration to the human in need of such treatment or prophylaxis, an effective amount of a compound as defined in the second aspect, or a pharmaceutically acceptable salt thereof.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

In order to use a compound as defined in the first or second aspect or a pharmaceutically acceptable salt thereof for the treatment or prophylaxis of humans and other mammals it is normally formulated in accordance with standard pharmaceutical practice as a pharmaceutical composition. Therefore in another aspect of the invention there is provided a pharmaceutical composition comprising a compound as defined in the first or second aspect, or a pharmaceutically acceptable salt thereof, adapted for use in human or veterinary medicine.

In order to use compounds as defined in the first or second aspect in therapy, they will normally be formulated into a pharmaceutical composition in accordance with standard pharmaceutical practice. The present invention also provides a pharmaceutical composition, which comprises a compound as defined in the first or second aspect, or a pharmaceutically acceptable salt thereof, and optionally a pharmaceutically acceptable excipient.

When used in the treatment or prophylaxis of pain, the compound as defined in the first or second aspect or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for Example sumatriptan, naratriptan, zolmitriptan, eletriptan, frovatriptan, almotriptan or rizatriptan; nicotinic acetyl choline (nACh) receptor modulators; glutamate receptor modulators, for Example modulators of the NR2B subtype; $EP_4^-$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. No. 5,474,995, U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/18374.

The invention thus provides, in a further aspect, a combination comprising a compound as defined in the first or second aspect or a pharmaceutically acceptable salt thereof together with a further therapeutic agent or agents.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 60% by weight, of the active material, depending on the method of administration. The dose of the compound as defined in the first or second aspect or a pharmaceutically acceptable salt thereof used in the treatment or prophylaxis of the aforementioned disorders will vary in the usual way with the seriousness of the disorders, the weight of the sufferer, and other similar factors. However, as a general guide suitable unit doses may be 0.05 to 1000 mg, more suitably 20 to 600 mg, and such unit doses may be administered more than once a day, for example two or three a day. Such therapy may extend for a number of weeks, months, years or even life.

A further aspect of the invention is a pharmaceutical composition comprising 0.05 to 1000 mg of a compound as defined in the first or second aspect or a pharmaceutically acceptable salt thereof, and 0 to 3 g more suitably 0 to 2 g of at least one pharmaceutically acceptable carrier.

All publications, including but not limited to patents and patent applications, cited in this specification are herein incorporated by reference as if each individual publication were specifically and individually indicated to be incorporated by reference herein as though fully set forth.

| Abbreviations | |
|---|---|
| aq.: | aqueous |
| DCM: | dichloromethane |
| DMSO: | dimethylsulfoxide |
| EtOAc: | ethyl acetate |

Abbreviations

| | |
|---|---|
| ES: | electrospray |
| MS: | mass spectrometry |
| MeCN: | acetonitrile |
| MDAP: | mass directed automated preparative liquid chromatography (for details see section 'Equipment'). |
| MeOH: | methanol |
| NMR: | nuclear magnetic resonance |
| sat.: | saturated |
| SAX: | strong anion exchange cartridge |
| SCX: | strong cation exchange chromatography |
| SPE: | solid phase extraction |
| THF: | tetrahydrofuran |
| TMS: | trimethylsilyl |
| HATU: | O-(7-azabenzotriazol-1-yl)-N,N,N',N'-tetramethyluronium hexafluorophosphate |
| HBTU: | O-benzotriazole-N,N,N',N'-tetramethyl-uronium-hexafluoro-phosphate |
| HOBT: | hydroxybenzotriazole |
| RT: | retention time |
| DPPF: | 1,1'-bis(diphenylphosphino)ferrocene |
| Pd$_2$(dba)$_3$: | tris(dibenzylideneacetone)dipalladium(0) |
| TFA: | trifluoroacetic acid |
| BOC: | t-butoxycarbonyl |
| DIPEA: | N,N-diisopropylethylamine |
| DMF: | N,N-dimethylformamide |
| EtOH: | ethanol |
| min: | minute(s) |
| h: | hour(s) |

Supporting Compounds

The preparation of a number of supporting compounds as defined in the first or second aspect are described below. In the procedures that follow, after each starting material, reference to an intermediate is typically provided. This is provided merely for assistance to the skilled chemist. The starting material may not necessarily have been prepared from the batch referred to.

Intermediate 1: Lithium 2-methyl-7-quinolinecarboxylate

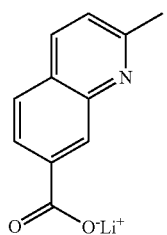

To a solution of 7-bromo-2-methylquinoline (400 mg, supplier Bioblocks Inc.) in THF (8 mL) under argon at −78° C. was added n-butyllithium (0.865 mL) dropwise. The reaction was stirred for 15 minutes at −78° C. before it was poured onto solid carbon dioxide in a beaker. The mixture was swirled until warmed to room temperature to prevent bumping, then the solvent was removed in vacuo to give the crude title compound (404 mg), which was used directly in subsequent reactions.

LCMS (low pH) RT 0.36 min, m/z (ES) 188 [M+H]$^+$

Intermediate 2: 8-Methyl-7-quinolinecarboxylic acid

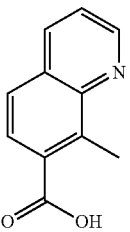

To a solution of concentrated sulfuric acid (21.74 ml) in water (16 ml), was added 3-amino-2-methylbenzoic acid (5 g; supplier Acros), 1,2,3-propanetriol (2.437 ml) and sodium iodide (0.104 g). The reaction mixture was heated to reflux for 2 hours at 150° C. Further 1,2,3-propanetriol (2.437 ml) was added and reaction mixture was refluxed for another two hours. The pH of the reaction mixture was adjusted to pH 3 by adding sodium hydroxide (12.5 M, 32.6 ml) then the mixture was filtered and the solid discarded. The aqueous phase was extracted with ethyl acetate and then the organic solvent was removed under vacuum to give crude product. This was dissolved in 1:1 DMSO & MeOH and purified by reverse phase chromatography and relevant fractions were combined and concentrated to afford the title compound (750 mg) as a white solid.

LCMS (low pH) RT 0.45 min, m/z (ES) 188 [M+H]$^+$

Intermediate 3: 4-Amino-3-methylbenzonitrile

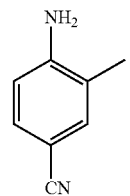

To an N-methyl-2-pyrrolidone (0.5 L) solution of 4-bromo-2-methylaniline (40 g) was added copper cyanide (38.5 g; 043 moli). The stirred mixture was heated at 200° C. for 2.5 hrs. The mixture was cooled at room temperature then water (1.9 L) and ammonia (0.5 L, 32%) were added. The mixture was extracted with ethyl acetate (2×1.2 L) and the combined organic phases then washed with a mixture of water/ammonia (0.5 L+0.2 L, 32%) and dried over Na$_2$SO$_4$. The solvent was evaporated under vacuum to give the title compound as a brown solid (27.5 g). This material was used in the next step without further purification.

Intermediate 4: 4-Cyano-2-methylbenzenesulfonyl chloride

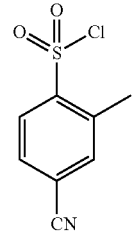

To an acetic acid (1.5 L) solution of 4-amino-3-methylbenzonitrile (may be prepared as described in Intermediate 3; 26 g) concentrated HCl (0.38 L) was added. The stirred reaction mixture was cooled at 0° C. and an aqueous solution of NaNO₂ (0.15 L, 13.6 g) was added maintaining the temperature below 5° C. for 45 min. Then the reaction mixture was slowly added (30 min) to a previously prepared saturated solution of SO₂ in acetic acid (2.7 L) containing copper chloride (105 g) maintaining the temperature at 10° C. The reaction temperature was raised to room temperature and stirred overnight. To the reaction mixture was added ice (1 kg) and water (3.5 L), stirring the suspension for 30 min. The organic layer was extracted with ethyl acetate (2×3 L). The combined organic phases was washed with a saturated solution of NaHCO₃ to neutral pH, then with water (1 L) and brine (0.8 L). The organic phase was dried over Na₂SO₄ and the solvent was evaporated and the resulting crude material was purified by flash chromatography (cyclohexane/ethyl acetate 85/15) to give the title compound (4 g).

¹H NMR (400 MHz, DMSO-d₆) δ 7.89 (1H, d, J=8.0 Hz), 7.63 (1H, s), 7.61 (1H, d, J=8.0 Hz), 2.58 (3H, s) ppm.

Intermediate 5: 1-{[4-(Trifluoromethyl)phenyl]sulfonyl}piperazine

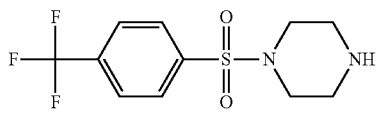 [SMILES: O=S(=O)(c1ccc(C(F)(F)F)cc1)N1CCNCC1]

To a solution of 1,1-dimethylethyl 1-piperazinecarboxylate (5.00 g, supplier Aldrich) in DCM (200 ml) was added DIPEA (9.85 ml) and then 4-(trifluoromethyl)benzenesulfonyl chloride (7.22 g, supplier Aldrich). The reaction mixture was stirred for 1.5 hours at room temperature. The reaction mixture was then reduced to dryness in vacuo, to give 1,1-dimethylethyl 4-{[4-(trifluoromethyl)phenyl]sulfonyl}-1-piperazinecarboxylate.

To a solution of this 1,1-dimethylethyl 4-{[4-(trifluoromethyl)phenyl]sulfonyl}-1-piperazinecarboxylate in 1,4-dioxane (100 ml), 4M HCl in 1,4-dioxane (50 ml) and 3 drops of distilled water was added. The reaction mixture was stirred overnight. Reaction mixture was then reduced to dryness in vacuo.

The residue was dissolved in DCM (200 ml) and washed with 2M NaOH (50 ml), twice. The organic layer was dried over dried magnesium sulphate, the insolubles removed by filtration, and filtrate reduced to dryness in vacuo to yield the title compound (6.60 g) as a pale yellow solid.

m/z (API-ES) 295 [M+H]⁺

1H NMR (400 MHz, CHLOROFORM-d) δ ppm 2.89-2.98 (m, 4H), 2.99-3.09 (m, 4H), 3.71 (s, 1H), 7.77-7.85 (m, 2H), 7.85-7.92 (m, 2H).

Intermediate 6: 4-{[(3S)-3-Methyl-1-piperazinyl]sulfonyl}benzonitrile

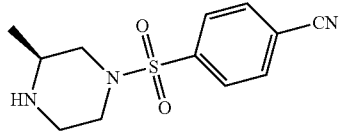 [SMILES: C[C@H]1CN(S(=O)(=O)c2ccc(C#N)cc2)CCN1]

To a solution of 1,1-dimethylethyl (2S)-2-methyl-1-piperazinecarboxylate (2.5 g, supplier Atlantic Scitech) and DIPEA (5.45 ml, 31.2 mmol) in dry dichloromethane (DCM) (60 ml) at 0° C. under argon was added 4-cyanobenzenesulfonyl chloride (2.64 g, 13.11 mmol) and the resulting clear solution stirred at 0° C. for 2 h. Saturated aqueous NaHCO₃ (100 mL) was added, the layers separated, then the organic layers washed with 2M aqueous HCl (100 mL) and passed through a hydrophobic frit. The solution in DCM was cooled to 0° C., then TFA (8.87 ml, 115 mmol) was added. The resulting very pale yellow solution was allowed to warm to room temperature over 1 h, then stirred for 18 h. Aqueous 2M NaOH (100 mL) was added cautiously with cooling (0° C.) and layers were separated. The organic layer was extracted with 1M aqueous HCl (3×30 mL). With cooling (0° C.), the combined acidic aqueous layers were adjusted to pH 7 by addition of solid NaOH, and then extracted with EtOAc (2×50 mL). The combined organic layers were washed with brine (30 mL), dried (MgSO₄), filtered and concentrated in vacuo to give the title compound as a white solid (2.35 g).

LCMS (low pH) RT 0.51 min, m/z (ES) 266 [M+H]⁺

Intermediate 7: 1,1-Dimethylethyl 4-[(4-bromo-2-methylphenyl)sulfonyl]-1-piperazinecarboxylate

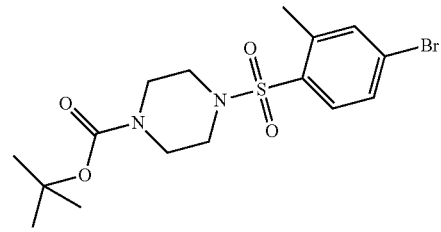 [SMILES: Cc1cc(Br)ccc1S(=O)(=O)N1CCN(C(=O)OC(C)(C)C)CC1]

To a solution of 1,1-dimethylethyl 1-piperazinecarboxylate (1.86 g, 9.99 mmol, supplier Aldrich) and DIPEA (2.62 ml, 14.98 mmol) in dry DCM (20 ml) at 0° C. under argon was added 4-bromo-2-methylbenzenesulfonyl chloride (2.96 g, 10.99 mmol) and the resulting yellow solution allowed to warm to rt, then stirred at rt for 18 h. Semi-saturated NH₄Cl (40 ml) was added, then the aq extracted with DCM (30 ml). The combined organics were passed through a hydrophobic frit, then concentrated in vacuo to give the title compound as a yellow gum that became a solid on standing (4.72 g).

LCMS (low pH) RT 1.37 min, m/z (ES) 319+321 [M-Boc+H]⁺

Intermediate 8: 1,1-Dimethylethyl 4-[(4-cyano-2-methylphenyl)sulfonyl]-1-piperazinecarboxylate

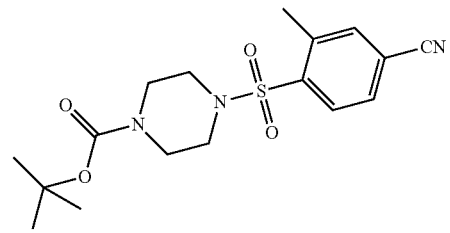 [SMILES: Cc1cc(C#N)ccc1S(=O)(=O)N1CCN(C(=O)OC(C)(C)C)CC1]

Argon was bubbled through a solution of 1,1-dimethylethyl 4-[(4-bromo-2-methylphenyl)sulfonyl]-1-piperazinecarboxylate (may be prepared as described in Intermediate 7; 4.19 g, 10 mmol) in dry DMF (40 ml) for 30 min, then Zn(CN)$_2$ (0.646 g, 5.50 mmol), Pd$_2$(dba)$_3$ (0.275 g, 0.300 mmol) and DPPF (0.333 g, 0.600 mmol) were added and the resulting brown solution stirred at 120° C. under argon for 2.5 h. The mixture was cooled to room temperature, concentrated in vacuo and the residue partitioned between DCM (100 ml) and water (100 ml). The aqueous was extracted with DCM (2×100 ml), then the combined organics passed through a hydrophobic frit. Concentration gave a dark brown residue (5.12 g). Flash chromatography (silica; Flash 40M; linear gradient 6-50% EtOAc in isohexane) gave the title compound (3.33 g) as a pale yellow solid.

LCMS (low pH) RT 1.21 min, m/z (ES) 266 [M-Boc+H]$^+$

Intermediate 9:
3-Methyl-4-(1-piperazinylsulfonyl)benzonitrile

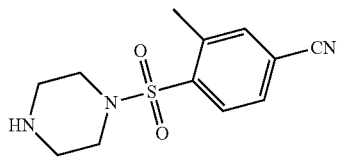 [SMILES: Cc1cc(C#N)ccc1S(=O)(=O)N1CCNCC1]

A solution of 1,1-dimethylethyl 4-[(4-cyano-2-methylphenyl)sulfonyl]-1-piperazinecarboxylate (may be prepared as described in Intermediate 8; 3.33 g, 9.11 mmol) and TFA (10 ml, 130 mmol) in dry dichloromethane (10 ml) was stirred at rt for 1 h, then concentrated in vacuo, azeotroping with toluene (25 ml) to give a brown oil. This was partitioned between DCM (50 ml) and sat. aq NaHCO$_3$ (50 ml), then the aqeuos layer extracted with DCM:EtOH (3:1, 40 ml). The combined organics were passed through a hydrophobic frit and concentrated in vacuo to give the title compound (2.59 g) as a yellow oil. The product became a pale yellow solid on standing.

LCMS (low pH) RT 0.56 min, m/z (ES) 266 [M+H]$^+$

Intermediate 10: 1,1-Dimethylethyl 4-({4-[(trifluoromethyl)oxy]phenyl}sulfonyl)-1-piperazinecarboxylate

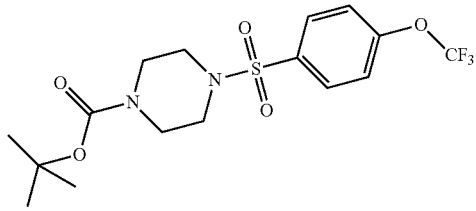 [SMILES: CC(C)(C)OC(=O)N1CCN(S(=O)(=O)c2ccc(OC(F)(F)F)cc2)CC1]

To a solution of 1,1-dimethylethyl 1-piperazinecarboxylate (5 g, 19.19 mmol, supplier Aldrich), in DCM (80 mL), DIPEA (5.03 mL, 28.8 mmol) was added under argon atmosphere at room temperature then 4-[(trifluoromethyl)oxy]benzenesulfonyl chloride (2.326 mL, 19.19 mmol) was added at 0° C. then ice bath was removed and the reaction mixture was stirred for 3 hrs. The reaction mixture was partitioned between DCM (30 ml) and sodium bicarbonate (2×20 ml). The organic phase was washed with HCl (2×20 ml) and water (2×20 ml), then it was dried using phase separator and DCM was removed under vacuum to give the title compound (5.5 g) as a yellow viscous liquid.

LCMS (high pH) RT 1.28 min, m/z (ES) 311 [M-Boc+H]$^+$

Intermediate 11: 1-({4-[(Trifluoromethyl)oxy]phenyl}sulfonyl)piperazine

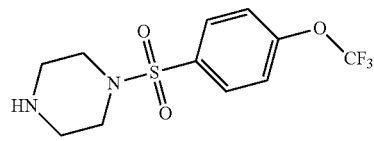 [SMILES: O=S(=O)(c1ccc(OC(F)(F)F)cc1)N1CCNCC1]

1,1-Dimethylethyl 4-({4-[(trifluoromethyl)oxy]phenyl}sulfonyl)-1-piperazinecarboxylate (may be prepared as described in Intermediate 10; 5.450 g, 13.28 mmol) was dissolved in DCM (80 ml) and then 4M hydrochloric acid in dioxane (33.2 mL, 133 mmol) was added at room temperature and the reaction mixture was stirred for two hours. The reaction mixture was partitioned between DCM and aqueous sodium bicarbonate (30 ml). The organic phase was washed with further sodium bicarbonate (2×20 ml) and water (2×20 ml). The aqueous phase (pH 1) was basified by adding sodium hydroxide then the aqueous phase was extracted with DCM (2×20 ml). The solvent was removed under vacuum to give the title compound (3.5 g) as a white solid.

LCMS (high pH) RT 0.91 min, m/z (ES) 311 [M+H]$^+$

Intermediate 12: 1,1-Dimethylethyl (2S)-4-[(4-cyano-2-methylphenyl)sulfonyl]-2-methyl-1-piperazinecarboxylate

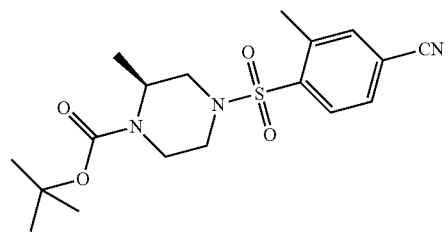 [SMILES: Cc1cc(C#N)ccc1S(=O)(=O)N1CCN(C(=O)OC(C)(C)C)[C@@H](C)C1]

To a solution of 1,1-dimethylethyl (2S)-2-methyl-1-piperazinecarboxylate (2.79 g, 13.91 mmol, supplier Antlantic Scitech) in DCM (80 mL), DIPEA (3.64 mL, 20.87 mmol) was added under argon atmosphere at room temperature then 4-cyano-2-methylbenzenesulfonyl chloride (3 g, 13.91 mmol) was added at 0° C. The ice bath was removed and the reaction mixture was stirred overnight. The reaction mixture was partitioned between DCM (30 ml) and aqueous sodium bicarbonate (2×20 ml). The organic phase was washed with HCl (2×20 ml) and water (2×20 ml) then it was dried (phase separator) and concentrated under vacuum to give the title compound (5.5 g) as a yellow viscous liquid.

LCMS (high pH) RT 1.24 min, m/z (ES) 280 [M-Boc+H]⁺

Intermediate 13: 3-Methyl-4-{[(3S)-3-methyl-1-piperazinyl]sulfonyl}benzonitrile

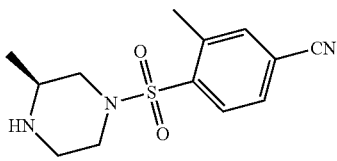 [SMILES: Cc1cc(C#N)ccc1S(=O)(=O)N1CCN[C@@H](C)C1]

1,1-Dimethylethyl (2S)-4-[(4-cyano-2-methylphenyl)sulfonyl]-2-methyl-1-piperazinecarboxylate (may be prepared as described in Intermediate 12; 5.52 g, 14.54 mmol) was dissolved in DCM (80 ml) and then 4M hydrochloric acid in dioxane (36.3 mL, 145 mmol) was added at room temperature and the reaction mixture was stirred for two hours. The solvent was removed under vacuum to give the title compound (4.0 g) as a white solid.

LCMS (high pH) RT 0.83 min, m/z (ES) 280 [M+H]⁺

Intermediate 14: (3S)-3-Methyl-1-({4-[(trifluoromethyl)oxy]phenyl}sulfonyl)piperazine

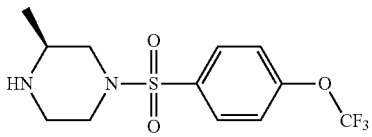

A mixture of (2S)-2-methylpiperazine (1 g, 9.98 mmol, supplier Aldrich) in tetrahydrofuran (8 mL) and 3M aqueous sodium hydroxide (6.66 mL, 19.97 mmol) was cooled to 0° C. before addition of 4-[(trifluoromethyl)oxy]benzenesulfonyl chloride (2.86 g, 10.98 mmol, supplier Aldrich) dropwise via a dropping funnel. After addition, the cool bath was removed and the reaction stirred at room temperature for 4 h before standing at room temperature for 17 h. The mixture was concentrated in vacuo and then the residue was taken up in water (15 mL) and DCM (20 mL) and the mixture stirred for 1 h. The layers were separated and then the organic phase extracted with 1M HCl (40 mL). The acidic aqueous phase was then basified to pH12 with solid NaOH and the mixture extracted with DCM (2×30 mL). The combined organic phase was dried (phase separator) and concentrated under vacuum to give the title compound (2.58 g) as a colourless oil.

LCMS (low pH) RT 0.78 min, m/z (ES) 325 [M+H]⁺

Intermediate 15: (3S)-1-({4-[(Difluoromethyl)oxy]phenyl}sulfonyl)-3-methylpiperazine hydrochloride

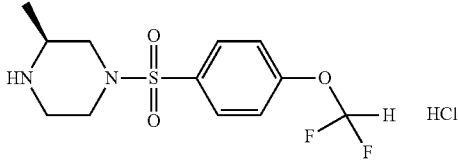 [SMILES: C[C@H]1CN(S(=O)(=O)c2ccc(OC(F)F)cc2)CCN1 ; Cl]

To a solution of 1,1-dimethylethyl (2S)-2-methyl-1-piperazinecarboxylate (1.5 g, 7.49 mmol, supplier Aldrich) and N,N-diisopropylethylamine (1.962 mL, 11.23 mmol) in dry DCM (20 mL) was added 4-[(difluoromethyl)oxy]benzenesulfonyl chloride (1.253 mL, 7.86 mmol, supplier Aldrich) dropwise. The solution was stirred at room temperature for 4 h and then left to stand for 16 h. The solution was washed with aqueous sodium bicarbonate (20 mL), 0.5 M HCl (20 mL) and brine (20 mL) before the organic phase was isolated by phase separator. To the solution was added hydrochloric acid (1.872 mL, 7.49 mmol) 4M in dioxane and the reaction stirred at room temperature for 3 h. LCMS showed only partial reaction, so further hydrochloric acid (1.872 mL, 7.49 mmol) 4M in dioxane was added and the reaction stirred for 21 h. The reaction mixture was then concentrated under vacuum to give the title compound (2.448 g) as a pale yellow solid.

LCMS (low pH) RT 0.63 min, m/z (ES) 307 [M+H]⁺

Intermediate 16 (3S)-3-Methyl-1-{[4-(trifluoromethyl)phenyl]sulfonyl}piperazine

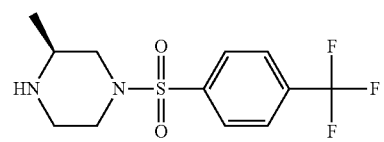 [SMILES: C[C@H]1CN(S(=O)(=O)c2ccc(C(F)(F)F)cc2)CCN1]

(2S)-2-Methylpiperazine (15 g, 150 mmol) was dissolved in tetrahydrofuran (300 mL) and the solution was cooled down to 0° C. Sodium hydroxide (150 mL, 449 mmol) was added, then 4-(trifluoromethyl)benzenesulfonyl chloride (40 g, 164 mmol) (dissolved in 200 ml THF) was added dropwise and the resulting mixture was stirred for 1 h. Further 4-(trifluoromethyl)benzenesulfonyl chloride (0.06 eq, 2.2 g) was added and mixture stirred for 10 min. The mixture was diluted with DCM (500 ml) and water (500 ml) and stirred for 5 min. The phases were separated, the aqueous layer was extracted with DCM (1000 ml) and the organic phases concentrated under reduced pressure. The residue was taken-up with 1 M HCl (500 ml) and washed with DCM in order to extracted impurities. The aqueous phase was basified to pH=9 with NaOH 3M, extracted with DCM (3×500 ml) and the combined organic phases dried over Na₂SO₄ before the solvent was removed under reduced pressure to give the title compound (30 g).

LCMS (low pH) m/z (ES) 309 [M+H]⁺

1H NMR (400 MHz, CDCl₃) δ 1.06 (d, J=7.2 Hz, 3H), 1.94 (t, J=10.4 Hz, 1H), (td, J=11.2, 4.0 Hz, 1H), 2.88-3.07 (m, 3H), 3.66 (m, 2H), 7.83 (d, J=8.4 Hz, 2H), 7.90 (d, J=8.4 Hz, 2H) ppm Compound 1: 7-[(((2S)-2-Methyl-4-{[4-(trifluoromethyl)phenyl]sulfonyl}-1-piperazinyl)carbonyl] quinoline

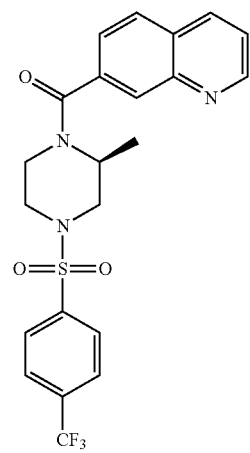 [SMILES: C[C@H]1CN(S(=O)(=O)c2ccc(C(F)(F)F)cc2)CCN1C(=O)c1ccc2cccnc2c1]

7-Quinolinecarboxylic acid (112 mg, 0.649 mmol) was weighed into a vial with the HATU (247 mg, 0.649 mmol), suspended in N,N-dimethylformamide (DMF) (2 ml) and treated with N,N-diisoproylethylamine (0.170 ml, 0.973 mmol). This mixture was stirred about 15 mins at ambient temperature. (3S)-3-methyl-1-{[4-(trifluoromethyl)phenyl] sulfonyl}piperazine (may be prepared in a similar manner as described in Intermediate 14; 100 mg, 0.324 mmol) was then added and stirring was continued. Stirring was stopped and the reaction mixture was left to stand overnight. The mixture was partitioned between DCM and sat aq. NaHCO₃ solution (10 ml each). The layers were separated (hydrophobic frit) and the aqueous was washed with further DCM (2×5 ml). The combined organic layers were concentrated to leave an orange gum (still contained DMF). This was diluted with a mixture of MeCN and DMSO to give ~1.8 ml orange solution which was purified by MDAP as two injections. The product fractions from the two runs were combined and concentrated to give the title compound as a colourless solid (119 mg).

LCMS (low pH) RT 0.96 min, m/z (ES) 464 [M+H]⁺

¹H NMR (400 MHz, DMSO-d₅) δ 8.99 (1H, dd, J=4.4, 1.6 Hz), 8.48 (1H, d, J=8.4 Hz), 8.09-8.04 (3H, m), 8.00-7.94 (3H, m), 6.64 (1H, dd, J=8.0, 4.4 Hz), 7.59 (1H, dd, J=8.0, 1.2 Hz) 5.0-3.3 (5H, m), 2.64 (1H, dd, J=12.0, 3.6 Hz), 2.48 (1H, m), 1.30 (3H, d, 6.8 Hz) ppm Compound 2: 8-Methyl-7-{[4-({4-[(trifluoromethyl) oxy]phenyl}sulfonyl)-1-piperazinyl] carbonyl}quinoline

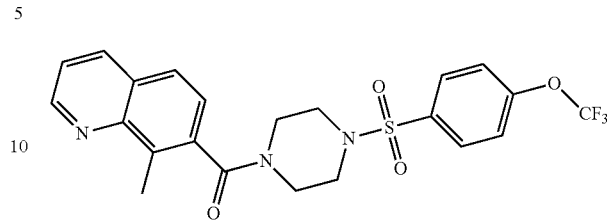

To the solution of 8-methyl-7-quinolinecarboxylic acid (may be prepared as described in Intermediate 2; 90 mg, 0.483 mmol) in N,N-Dimethylformamide (DMF) (2 ml), HATU (193 mg, 0.508 mmol) was added at room temperature. The reaction was stirred for 20 min and then 1-({4-[(trifluoromethyl)oxy]phenyl}sulfonyl)piperazine (may be prepared as described in Intermediate 11; 150 mg, 0.483 mmol) was added followed by DIPEA (0.211 ml, 1.209 mmol) and the reaction mixture was stirred for 3 hours. The reaction mixture was poured into the separating funnel and partitioned between ethyl acetate (25 ml) and sodium hydroxide (15 ml). The organic phase was washed with sodium hydroxide (2×10 ml), water (2×10 ml) and brine (10 mL) before it was dried using phase separator and the solvent was removed under vacuum. The crude product was purified by MDAP to give the title compound as a white solid (115 mg).
LCMS (low pH) RT 1.03 min, m/z (ES) 480 [M+H]⁺
¹H NMR (400 MHz, CDCl₃) δ 8.99 (1H, dd, J=4.0, 1.6 Hz), 8.14 (1H, dd, J=8.4, 1.6 Hz), 7.80 (2H, d, J=8.4 Hz), 7.71 (1H, d, J=8.4 Hz), 7.47 (1H, dd, J=8.4, 4.4 Hz), 7.40 (2H, d, J=8.4 Hz), 7.26 (1H, d, J=8.4 Hz), 4.08-3.91 (2H, m), 3.37 (2H, t, J=4.8 Hz), 3.27-3.12 (2H, m), 3.02-2.86 (2H, m), 2.69 (3H, s) ppm
The following compounds were prepared in a similar manner as compound 1 and 2 from the corresponding starting materials:

| Compound no. | Structure | Name | Characterisation: LCMS |
|---|---|---|---|
| 3 | 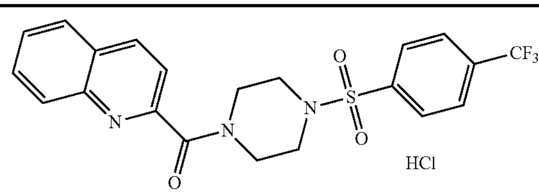 | 2-[(4-{[4-(Trifluoromethyl) phenyl]sulfonyl}-1-piperazinyl)carbonyl] quinoline hydrochloride | Low pH (5 in) RT = 2.88 min; m/z 450 [MH]⁺ |
| 4 | 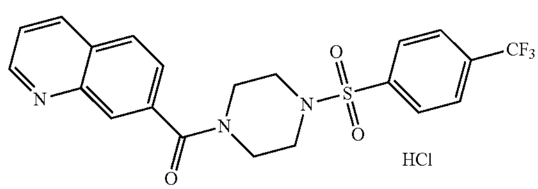 [SMILES: O=C(c1ccc2cccnc2c1)N1CCN(S(=O)(=O)c2ccc(C(F)(F)F)cc2)CC1 ; Cl] | 7-[(4-{[4-(Trifluoromethyl) phenyl]sulfonyl}-1-piperazinyl)carbonyl] quinoline hydrochloride | Low pH (5 in) RT = 2.41 min; m/z 450 [MH]⁺ |
| 5 | 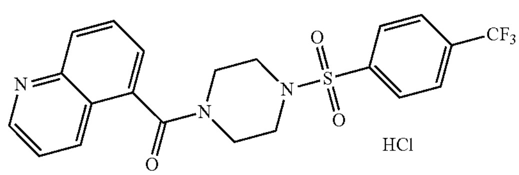 [SMILES: O=C(c1cccc2ncccc12)N1CCN(S(=O)(=O)c2ccc(C(F)(F)F)cc2)CC1 ; Cl] | 5-[(4-{[4-(Trifluoromethyl) phenyl]sulfonyl}-1-piperazinyl)carbonyl] quinoline hydrochloride | Low pH RT = 1.00 min; m/z 450 [MH]⁺ |

-continued

| Compound no. | Structure | Name | Characterisation: LCMS |
|---|---|---|---|
| 6 | 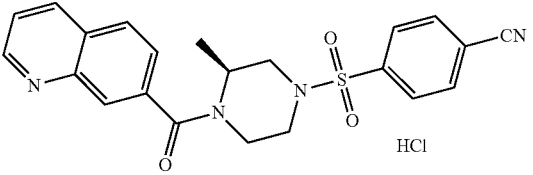 [SMILES: C[C@H]1CN(S(=O)(=O)c2ccc(C#N)cc2)CCN1C(=O)c1ccc2cccnc2c1 ; Cl] | 4-{[(3S)-3-Methyl-4-(7-quinolinylcarbonyl)-1-piperazinyl]sulfonyl} benzonitrile hydrochloride | Low pH RT = 0.83 min; m/z 421 [MH]$^+$ |
| 7 | 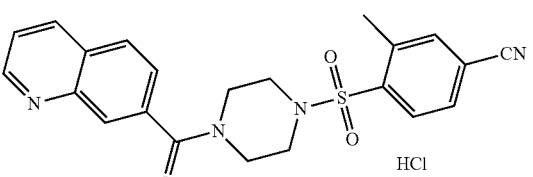 | 3-Methyl-4-{[4-(7-quinolinylcarbonyl)-1-piperazinyl]sulfonyl} benzonitrile hydrochloride | Low pH RT = 0.85 min; m/z 421 [MH]$^+$ |
| 8 | 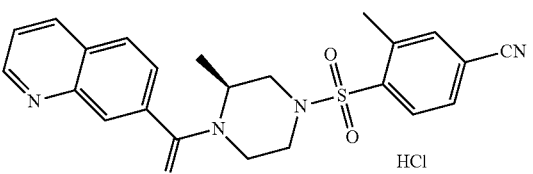 | 3-Methyl-4-{[(3S)-3-methyl-4-(7-quinolinylcarbonyl)-1-piperazinyl]sulfonyl} benzonitrile hydrochloride | Low pH RT = 0.86 min; m/z 435 [MH]$^+$ |
| 9 | 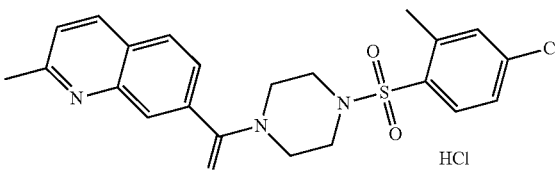 | 3-Methyl-4-({4-[(2-methyl-7-quinolinyl)carbonyl]-1-piperazinyl}sulfonyl) benzonitrile hydrochloride | Low pH RT = 0.75 min; m/z 435 [MH]$^+$ |
| 10 | 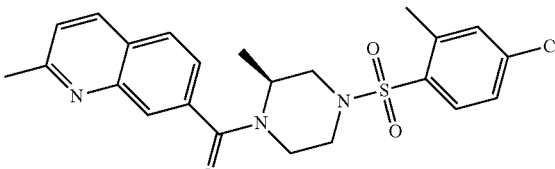 | 3-Methyl-4-({(3S)-3-methyl-4-[(2-methyl-7-quinolinyl)carbonyl]-1-piperazinyl}sulfonyl) benzonitrile | Low pH RT = 0.78 min; m/z 449 [MH]$^+$ |
| 11 | 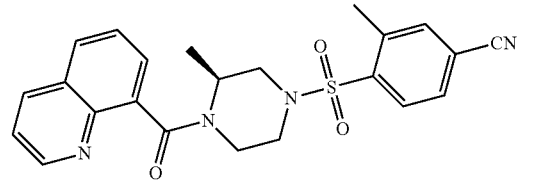 [SMILES: Cc1cc(C#N)ccc1S(=O)(=O)N1CCN(C(=O)c2cccc3cccnc23)[C@@H](C)C1] | 3-Methyl-4-{[(3S)-3-methyl-4-(8-quinolinylcarbonyl)-1-piperazinyl]sulfonyl} benzonitrile | high pH RT = 1.03 min; m/z 435 [MH]$^+$ |
| 12 | 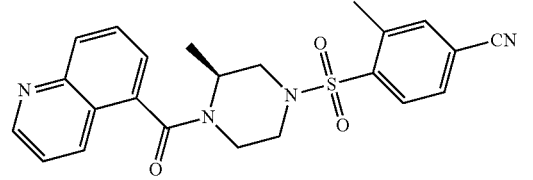 [SMILES: Cc1cc(C#N)ccc1S(=O)(=O)N1CCN(C(=O)c2cccc3ncccc23)[C@@H](C)C1] | 3-Methyl-4-{[(3S)-3-methyl-4-(5-quinolinylcarbonyl)-1-piperazinyl]sulfonyl} benzonitrile | high pH RT = 0.86 min; m/z 435 [MH]$^+$ |
| 13 | 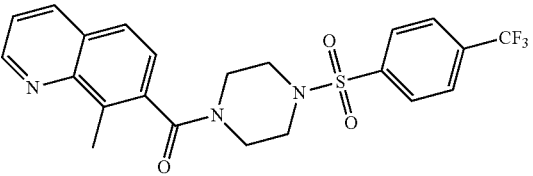 [SMILES: Cc1c(C(=O)N2CCN(S(=O)(=O)c3ccc(C(F)(F)F)cc3)CC2)ccc2cccnc12] | 8-Methyl-7-[(4-{[4-(trifluoromethyl)phenyl]sulfonyl}-1-piperazinyl)carbonyl] quinoline | high pH RT = 1.10 min; m/z 464 [MH]$^+$ |

| Compound no. | Structure | Name | Characterisation: LCMS |
|---|---|---|---|
| 14 | 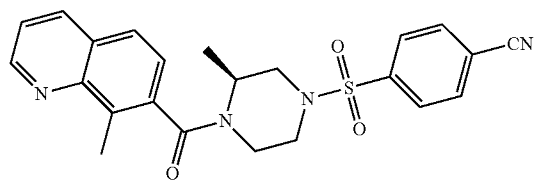 [SMILES: Cc1c(C(=O)N2CCN(S(=O)(=O)c3ccc(C#N)cc3)C[C@@H]2C)ccc2cccnc12] | 4-({(3S)-3-Methyl-4-[(8-methyl-7-quinolinyl)carbonyl]-1-piperazinyl}sulfonyl)benzonitrile | high pH RT = 0.98 min; m/z 435 [MH]+ |
| 15 | 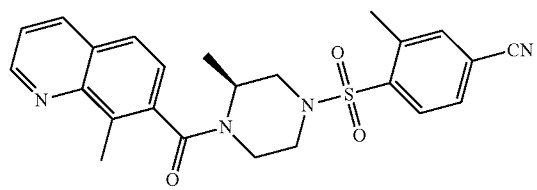 [SMILES: Cc1cc(C#N)ccc1S(=O)(=O)N1CCN(C(=O)c2ccc3cccnc3c2C)[C@@H](C)C1] | 3-Methyl-4-({(3S)-3-methyl-4-[(8-methyl-7-quinolinyl)carbonyl]-1-piperazinyl}sulfonyl)benzonitrile | high pH RT = 1.04 min; m/z 449 [MH]+ |
| 16 | 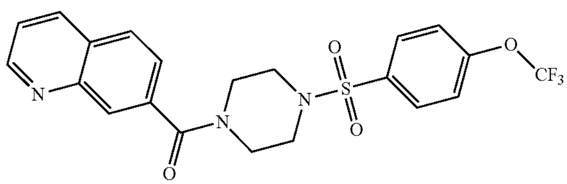 [SMILES: O=C(c1ccc2cccnc2c1)N1CCN(S(=O)(=O)c2ccc(OC(F)(F)F)cc2)CC1] | 7-{[4-({4-[(Trifluoromethyl)oxy]phenyl}sulfonyl)-1-piperazinyl]carbonyl}quinoline | low pH RT = 1.04 min; m/z 466 [MH]+ |
| 17 | 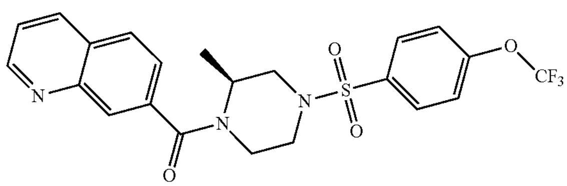 [SMILES: C[C@H]1CN(S(=O)(=O)c2ccc(OC(F)(F)F)cc2)CCN1C(=O)c1ccc2cccnc2c1] | 7-{[(2S)-2-Methyl-4-({4-[(trifluoromethyl)oxy]phenyl}sulfonyl)-1-piperazinyl]carbonyl}quinoline | low pH RT = 1.00 min; m/z 480 [MH]+ |
| 18 | 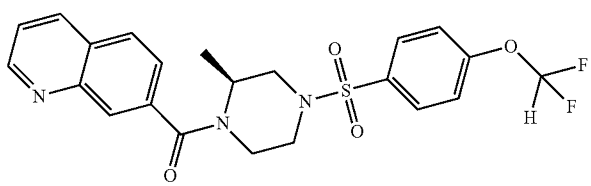 [SMILES: C[C@H]1CN(S(=O)(=O)c2ccc(OC(F)F)cc2)CCN1C(=O)c1ccc2cccnc2c1] | 7-{[(2S)-4-({4-[(Difluoromethyl)oxy]phenyl}sulfonyl)-2-methyl-1-piperazinyl]carbonyl}quinoline | low pH RT = 0.89 min; m/z 461 [MH]+ |
| 19 | 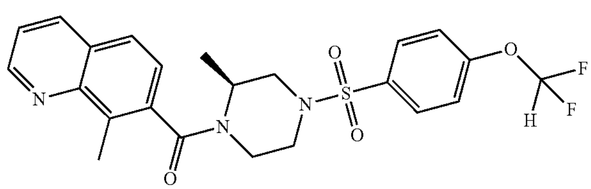 | 7-{[(2S)-4-({4-[(Difluoromethyl)oxy]phenyl}sulfonyl)-2-methyl-1-piperazinyl]carbonyl}-8-methylquinoline | low pH RT = 0.96 min; m/z 461 [MH]+ |

Compound 20: 8-[(((2S)-2-Methyl-4-{[4-(trifluoromethyl)phenyl]sulfonyl}-1-piperazinyl)carbonyl]isoquinoline hydrochloride

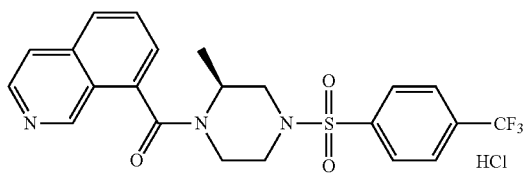 [SMILES: C[C@H]1CN(S(=O)(=O)c2ccc(C(F)(F)F)cc2)CCN1C(=O)c1cccc2ccncc12 ; Cl]

To a solution of (3S)-3-methyl-1-{[4-(trifluoromethyl)phenyl]sulfonyl}piperazine (may be prepared in a similar manner as described in Intermediate 16; 50 mg, 0.162 mmol) and 8-isoquinolinecarboxylic acid (28.1 mg, 0.162 mmol) in N,N-Dimethylformamide (DMF) (5 mL), was added HOBT (27.3 mg, 0.178 mmol), n-ethylmorpholine (0.045 mL, 0.357 mmol), and HBTU (67.7 mg, 0.178 mmol) in sequence. Solvent was removed under vacuum to leave an oil which was dissolved in 1.7 ml of 1:1 DMSO/MeCN and purified by MDAP. Relevant fractions were combined and concentrated to leave a clear oil (32 mg). The oil was dissolved in 5 ml THF and 0.05 ml of 5M aqueous HCl was added. The solvent was removed to give the title compound as a white solid (35 mg).

LCMS (low pH) RT 0.92 min, m/z (ES) 464 [M+H]+

$^1$H NMR (400 MHz, MeOD) rotameric mixture δ 9.10 (1H, m), 8.50 (1H, m), 8.1-7.88 (6H, m), 7.83 (1H, m), 7.59 (1H, m), 5.25-4.55 (3H, m), 4.0-3.4 (4H, m), 2.8-2.1 (2H, m), 1.6-1.1 (3H, m) ppm The following compounds were prepared in a similar manner as compound 20 from the corresponding starting materials:

| Compound no. | Structure | Name | Characterisation: LCMS |
|---|---|---|---|
| 21 | 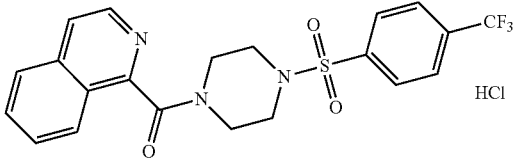 [SMILES: O=C(c1nccc2ccccc12)N1CCN(S(=O)(=O)c2ccc(C(F)(F)F)cc2)CC1 ; Cl] | 1-[(4-{[4-(Trifluoromethyl)phenyl]sulfonyl}-1-piperazinyl)carbonyl]isoquinoline hydrochloride | low pH RT = 1.13 min; m/z 450 [MH]⁺ |
| 22 | 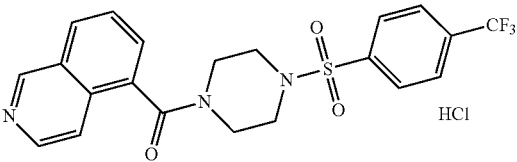 [SMILES: O=C(c1cccc2cnccc12)N1CCN(S(=O)(=O)c2ccc(C(F)(F)F)cc2)CC1 ; Cl] | 5-[(4-{[4-(Trifluoromethyl)phenyl]sulfonyl}-1-piperazinyl)carbonyl]isoquinoline hydrochloride | low pH RT = 0.91 min; m/z 450 [MH]⁺ |
| 23 | 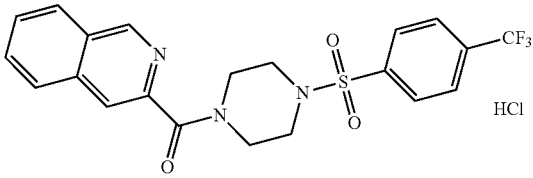 [SMILES: O=C(c1cc2ccccc2cn1)N1CCN(S(=O)(=O)c2ccc(C(F)(F)F)cc2)CC1 ; Cl] | 3-[(4-{[4-(Trifluoromethyl)phenyl]sulfonyl}-1-piperazinyl)carbonyl]isoquinoline hydrochloride | low pH RT = 1.14 min; m/z 450 [MH]⁺ |
| 24 | 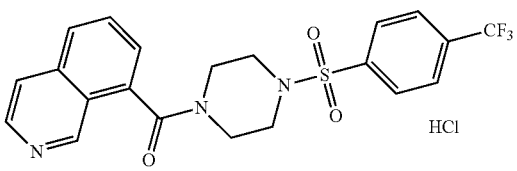 [SMILES: O=C(c1cccc2ccncc12)N1CCN(S(=O)(=O)c2ccc(C(F)(F)F)cc2)CC1 ; Cl] | 8-[(4-{[4-(Trifluoromethyl)phenyl]sulfonyl}-1-piperazinyl)carbonyl]isoquinoline hydrochloride | low pH RT = 0.95 min; m/z 450 [MH]⁺ |
| 25 | 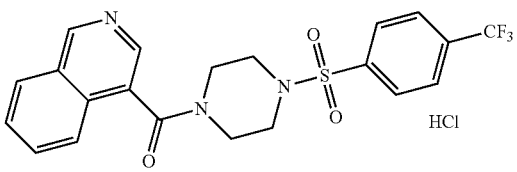 [SMILES: O=C(c1cncc2ccccc12)N1CCN(S(=O)(=O)c2ccc(C(F)(F)F)cc2)CC1 ; Cl] | 4-[(4-{[4-(Trifluoromethyl)phenyl]sulfonyl}-1-piperazinyl)carbonyl]isoquinoline hydrochloride | low pH RT = 1.04 min; m/z 450 [MH]⁺ |
| 26 | 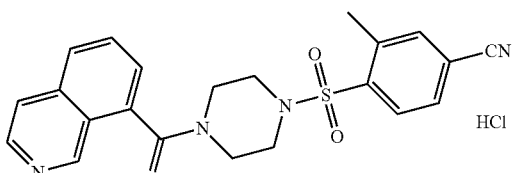 | 4-{[4-(8-Isoquinolinylcarbonyl)-1-piperazinyl]sulfonyl}-3-methylbenzonitrile hydrochloride | low pH RT = 0.77 min; m/z 421 [MH]⁺ |
| 27 | 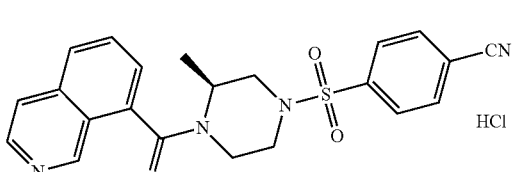 | 4-{[(3S)-4-(8-Isoquinolinylcarbonyl)-3-methyl-1-piperazinyl]sulfonyl}benzonitrile hydrochloride | low pH RT = 0.76 min; m/z 421 [MH]⁺ |
| 28 | 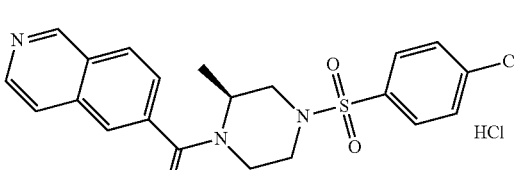 | 4-{[(3S)-4-(6-Isoquinolinylcarbonyl)-3-methyl-1-piperazinyl]sulfonyl}benzonitrile hydrochloride | low pH RT = 0.67 min; m/z 421 [MH]⁺ |

| Compound no. | Structure | Name | Characterisation: LCMS |
|---|---|---|---|
| 29 | 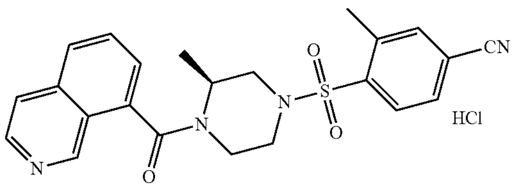 [SMILES: Cc1cc(C#N)ccc1S(=O)(=O)N1CCN(C(=O)c2cccc3ccncc23)[C@@H](C)C1 ; Cl] | 4-{[(3S)-4-(8-Isoquinolinylcarbonyl)-3-methyl-1-piperazinyl]sulfonyl}-3-methylbenzonitrile hydrochloride | low pH RT = 0.79 min; m/z 435 [MH]+ |

The following compounds are commercially available:

| Compound no. | Structure | Name | Characterisation: LCMS |
|---|---|---|---|
| 30 (Suppliers: AKos, Enamine, Abiner Aurora, Ryan Scientific) | 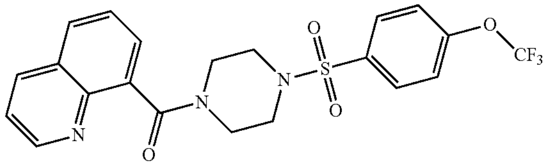 [SMILES: O=C(c1cccc2cccnc12)N1CCN(S(=O)(=O)c2ccc(OC(F)(F)F)cc2)CC1] | 8-{[4-({4-[(Trifluoromethyl)oxy]phenyl}sulfonyl)-1-piperazinyl]carbonyl}quinoline | Low pH RT = 1.04 min; m/z 466 [MH]+ |
| 31 (Suppliers: Aurora, AKos) | 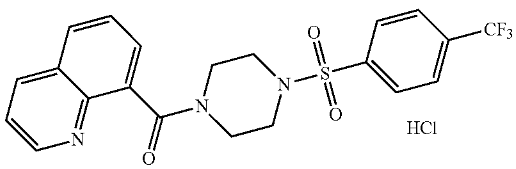 [SMILES: O=C(c1cccc2cccnc12)N1CCN(S(=O)(=O)c2ccc(C(F)(F)F)cc2)CC1 ; Cl] | 8-[(4-{[4-(Trifluoromethyl)phenyl]sulfonyl}-1-piperazinyl)carbonyl]quinoline hydrochloride | Low pH RT = 1.08 min; m/z 450 [MH]+ |

Prophetic Compounds:
The following compounds may be prepared in a similar manner as the compounds described hereinbefore.

| Compound no. | Structure | Name |
|---|---|---|
| 32 | 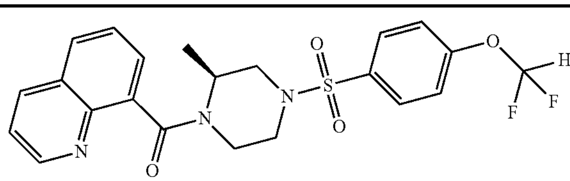 | 8-{[(2S)-4-({4-[(Difluoromethyl)oxy]phenyl}sulfonyl)-2-methyl-1-piperazinyl]carbonyl}quinoline |
| 33 | 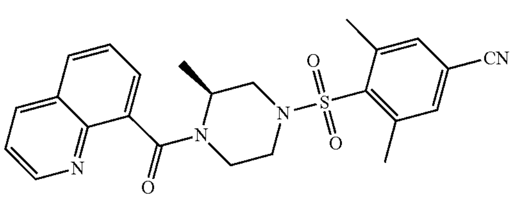 [SMILES: Cc1cc(C#N)cc(C)c1S(=O)(=O)N1CCN(C(=O)c2cccc3cccnc23)[C@@H](C)C1] | 3,5-Dimethyl-4-{[(3S)-3-methyl-4-(8-quinolinylcarbonyl)-1-piperazinyl]sulfonyl}benzonitrile |
| 34 | 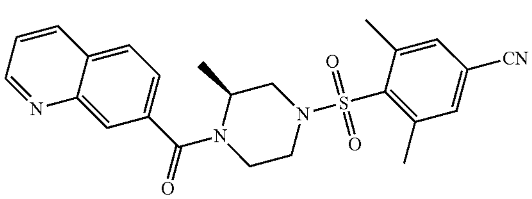 [SMILES: Cc1cc(C#N)cc(C)c1S(=O)(=O)N1CCN(C(=O)c2ccc3cccnc3c2)[C@@H](C)C1] | 3,5-Dimethyl-4-{[(3S)-3-methyl-4-(7-quinolinylcarbonyl)-1-piperazinyl]sulfonyl}benzonitrile |

-continued

| Compound no. | Structure | Name |
|---|---|---|
| 35 | 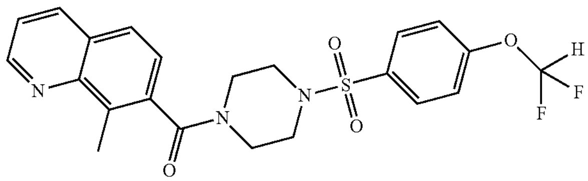 [SMILES: Cc1c(C(=O)N2CCN(S(=O)(=O)c3ccc(OC(F)F)cc3)CC2)ccc2cccnc12] | 7-{[4-({4-[(Difluoromethyl)oxy]phenyl}sulfonyl)-1-piperazinyl]carbonyl)-8-methylquinoline |
| 36 | 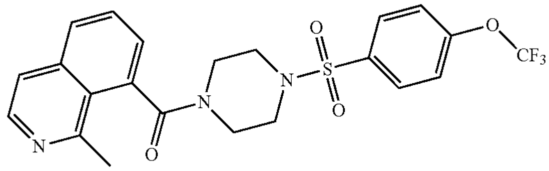 [SMILES: Cc1nccc2cccc(C(=O)N3CCN(S(=O)(=O)c4ccc(OC(F)(F)F)cc4)CC3)c12] | 1-Methyl-8-{[4-({4-[(trifluoromethyl)oxy]phenyl}sulfonyl)-1-piperazinyl]carbonyl}isoquinoline |
| 37 | 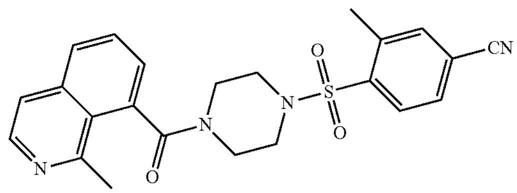 [SMILES: Cc1cc(C#N)ccc1S(=O)(=O)N1CCN(C(=O)c2cccc3ccnc(C)c23)CC1] | 3-Methyl-4-({4-[(1-methyl-8-isoquinolinyl)carbonyl]-1-piperazinyl}sulfonyl)benzonitrile |
| 38 | 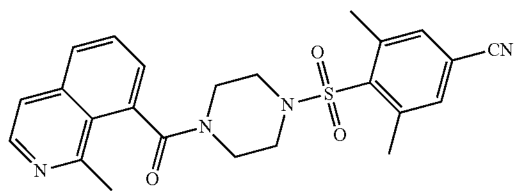 [SMILES: Cc1cc(C#N)cc(C)c1S(=O)(=O)N1CCN(C(=O)c2cccc3ccnc(C)c23)CC1] | 3,5-Dimethyl-4-({4-[(1-methyl-8-isoquinolinyl)carbonyl]-1-piperazinyl}sulfonyl)benzonitrile |
| 39 | 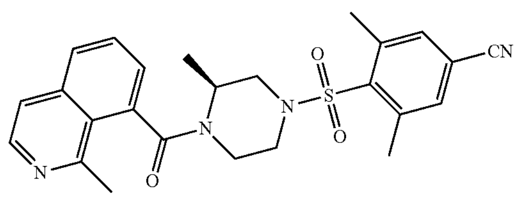 [SMILES: Cc1cc(C#N)cc(C)c1S(=O)(=O)N1CCN(C(=O)c2cccc3ccnc(C)c23)[C@@H](C)C1] | 3,5-Dimethyl-4-({(3S)-3-methyl-4-[(1-methyl-8-isoquinolinyl)carbonyl]-1-piperazinyl}sulfonyl)benzonitrile |
| 40 | 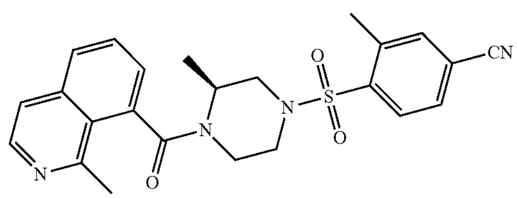 [SMILES: Cc1cc(C#N)ccc1S(=O)(=O)N1CCN(C(=O)c2cccc3ccnc(C)c23)[C@@H](C)C1] | 3-Methyl-4-({(3S)-3-methyl-4-[(1-methyl-8-isoquinolinyl)carbonyl]-1-piperazinyl}sulfonyl)benzonitrile |
| 41 | 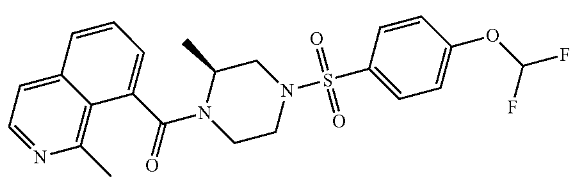 [SMILES: Cc1nccc2cccc(C(=O)N3CCN(S(=O)(=O)c4ccc(OC(F)F)cc4)C[C@@H]3C)c12] | 8-{[(2S)-4-({4-[(Difluoromethyl)oxy]phenyl}sulfonyl)-2-methyl-1-piperazinyl]carbonyl}-1-methylisoquinoline |
| 42 | 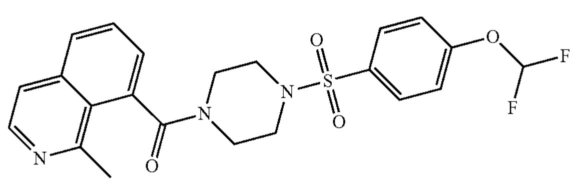 [SMILES: Cc1nccc2cccc(C(=O)N3CCN(S(=O)(=O)c4ccc(OC(F)F)cc4)CC3)c12] | 8-{[4-({4-[(Difluoromethyl)oxy]phenyl}sulfonyl)-1-piperazinyl]carbonyl}-1-methylisoquinoline |

| Compound no. | Structure | Name |
|---|---|---|
| 43 | 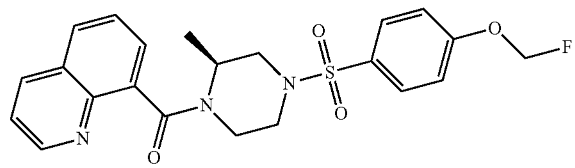 [SMILES: C[C@H]1CN(S(=O)(=O)c2ccc(OCF)cc2)CCN1C(=O)c1cccc2cccnc12] | 8-{[(2S)-4-({4-[(Fluoromethyl)oxy]phenyl}sulfonyl)-2-methyl-1-piperazinyl]carbonyl}quinoline |
| 44 | 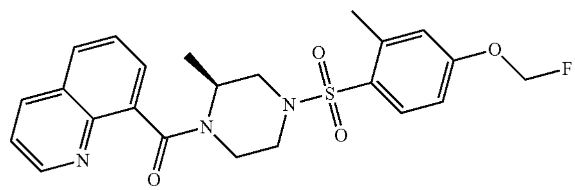 [SMILES: Cc1cc(OCF)ccc1S(=O)(=O)N1CCN(C(=O)c2cccc3cccnc23)[C@@H](C)C1] | 8-{[(2S)-4-({4-[(Fluoromethyl)oxy]-2-methylphenyl}sulfonyl)-2-methyl-1-piperazinyl]carbonyl}quinoline |
| 45 | 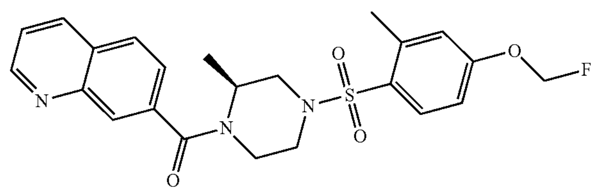 [SMILES: Cc1cc(OCF)ccc1S(=O)(=O)N1CCN(C(=O)c2ccc3cccnc3c2)[C@@H](C)C1] | 7-{[(2S)-4-({4-[(Fluoromethyl)oxy]-2-methylphenyl}sulfonyl)-2-methyl-1-piperazinyl]carbonyl}quinoline |
| 46 | 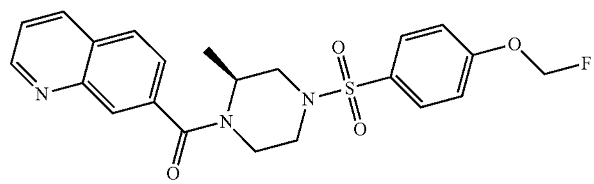 [SMILES: C[C@H]1CN(S(=O)(=O)c2ccc(OCF)cc2)CCN1C(=O)c1ccc2cccnc2c1] | 7-{[(2S)-4-({4-[(Fluoromethyl)oxy]phenyl}sulfonyl)-2-methyl-1-piperazinyl]carbonyl}quinoline |
| 47 | 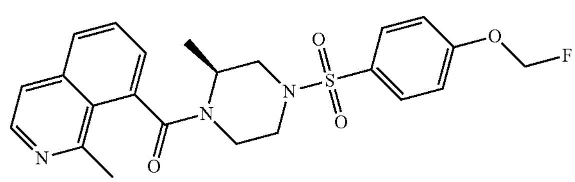 [SMILES: Cc1nccc2cccc(C(=O)N3CCN(S(=O)(=O)c4ccc(OCF)cc4)C[C@@H]3C)c12] | 8-{[(2S)-4-({4-[(Fluoromethyl)oxy]phenyl}sulfonyl)-2-methyl-1-piperazinyl]carbonyl}-1-methylisoquinoline |

Equipment:

$^1$H NMR Spectra

Chemical shifts are expressed in parts per million (ppm, units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Mass-Directed Automated HPLC/Mass-Directed Automated Preparation (MDAP)

Where indicated in the above compounds, purification by mass-directed automated HPLC was carried out using the following apparatus and conditions:

Hardware

Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector Software Waters MassLynx version 4 SP2

Column

The columns used are Waters Atlantis, the dimensions of which are 19 mm×100 mm (small scale) and 30 mm×100 mm (large scale). The stationary phase particle size is 5 μm.

Solvents

A: Aqueous solvent=Water+0.1% Formic Acid
B: Organic solvent=Acetonitrile+0.1% Formic Acid
Make up solvent=Methanol:Water 80:20
Needle rinse solvent=Methanol Methods There are five methods used depending on the analytical retention time of the compound of interest. They have a 13.5-minute runtime, which comprises of a 10-minute gradient followed by a 3.5 minute column flush and re-equilibration step.

Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow Rate

All of the above methods have a flow rate of either 20 mls/min (Small Scale) or 40 mls/min (Large Scale).

High pH Focused Preparative Open Access LC/MS (High pH MDAP)

Column

The columns used are Xbridge C18 column, the dimensions of which are 19 mm×100 mm (small scale) and 30 mm×150 mm (large scale). The stationary phase particle size is 5 μm.

Solvents

A: Aqueous solvent=10 mM ammonium bicarbonate in water adjusted to pH10 with ammonia solution B: Organic solvent=Acetonitrile Methods There are five methods used depending on the analytical retention time of the compound of interest. The user can select a 15 minute or 25 minute runtime.

Large/Small Scale Method A: 99% A to 1% A in B
Large/Small Scale Method B=85% A to 1% A in B
Large/Small Scale Method C=70% A to 1% A in B
Large/Small Scale Method D=50% A to 1% A in B
Large/Small Scale Method E=20% A to 1% A in B Flow Rate All of the above methods have a flow rate of either 20 mls/min (Small Scale) or 40 mls/min (Large Scale).

UV Detection

The UV detection was an averaged signal from wavelength of 210 nm to 350 nm and mass spectra were recorded on a mass spectrometer using alternate-scan positive and negative mode electrospray ionization.

Liquid Chromatography/Mass Spectrometry

Analysis of the above compounds by Liquid Chromatography/Mass Spectrometry (LC/MS) was carried out using the following apparatus and conditions:

Hardware

Waters Acquity Binary Solvent Manager
Waters Acquity Sample Manager
Waters Acquity PDA
Waters ZQ Mass Spectrometer
Sedere Sedex 75

Software

Waters MassLynx version 4.1

Column

The column used is a Waters Acquity BEH UPLC C18, the dimensions of which are 2.1 mm×50 mm. The stationary phase particle size is 1.7 μm.

Solvents

A: Aqueous solvent=Water+0.1% Formic Acid
B: Organic solvent=Acetonitrile+0.1% Formic Acid
Weak Wash=1:1 Methanol:Water
Strong Wash=Water Method The generic method used has a 2 minute runtime.

| Time/min | % B |
| --- | --- |
| 0 | 3 |
| 0.1 | 3 |
| 1.5 | 97 |
| 1.9 | 97 |
| 2.0 | 3 |

The above method has a flow rate of 1 ml/min.

The injection volume for the generic method is 0.5 ul

The column temperature is 40° C.

The UV detection range is from 220 to 330 nm

5 Minute Method Low pH Formic Acid Generic Analytical HPLC Open Access LC/MS

Where stated, a 5 minute LCMS run was used instead of the usual 2 min run. The HPLC analysis was conducted on a Sunfire C18 column (30 mm×4.6 mm i.d. 3.5 μm packing diameter) at 30 degrees centigrade.

The solvents employed were:
A=0.1% v/v solution of Formic Acid in Water.
B=0.1% v/v solution of Formic Acid in Acetonitrile.

The gradient employed was:

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

High pH Liquid Chromatography/Mass Spectroscopy

The analysis was conducted on an Acquity UPLC BEH C18 column (2.1 mm×50 mm i.d. 1.7 μm packing diameter) at 40 degrees centigrade.

The solvents employed were:
A=10 mM Ammonium Bicarbonate in water adjusted to pH 10 with ammonia solution
B=Acetonitrile The gradient employed was from 1-100% B in A over a period of 2 minutes The UV detection was an averaged signal from wavelength of 220 nm to 350 nm and mass spectra were recorded on a mass spectrometer using alternate-scan positive and negative mode electrospray ionization Alternatively, the analysis was conducted on an XBridge C18 column (4.6 mm×50 mm i.d. 3.5 μm packing diameter) at 30 degrees centigrade.

The solvents employed were:
A=10 mM Ammonium Bicarbonate in water adjusted to pH 10 with ammonia solution
B=Acetonitrile The gradient employed was from 1-97% B in A over a period of 5 minutes The UV detection was an averaged signal from wavelength of 220 nm to 350 nm and mass spectra were recorded on a mass spectrometer using alternate-scan positive and negative mode electrospray ionization Biotage SP4®

Biotage-SP4® is an automated purification system. It uses preloaded silica gel columns. The user applies their material to the top of the column and chooses solvents, gradients, flow rates, column size, collection method and eluting volumes.

The Biotage SP4® may also be used in reverse phase mode using a C18 column. The user applies their material to the top of the column and runs a standard gradient from 0-100% (0.1% formic acid in acetonitrile) in (0.1% formic acid in water). The user chooses the flow rate, column size, collection method and eluting volumes.

Phase Separators (Hydrophobic Frit)

Phase separators are a range of ISOLUTE® columns fitted with an optimized frit material that easily separates aqueous phase from chlorinated solvents under gravity.

SCX—Strong Cation Exchange Cartridge

Where indicated in the compounds, an SCX cartridge was used as part of the compound purification process. Typically an ISOLUTE SCX-2 cartridge was used. ISOLUTE SCX-2 is a silica-based sorbent with a chemically bonded propylsulfonic acid functional group.

ISOLUTE SCX-2 Chemical Data

Base Material: Silica, 50 μm
Functional Group: Propylsulfonic acid
Capacity: 0.6 meq/g
Counter Ion: Proton SAX—Strong Anion Exchange Cartridge Where indicated in the compounds, an SAX cartridge was used as part of the compound purification process. Typically an ISOLUTE SAX cartridge was used. ISOLUTE SAX is a silica-based sorbent with a chemically bonded quaternary trimethylaminopropyl chloride functional group.

Pharmacological Data

Assay 1 (N-Type):

Compounds as defined in the first or second aspect may be tested for in vitro biological activity in the hCa$_v$2.2 assay (N-type) in accordance with the following studies:

Methods

Cell Biology

Stable cell lines expressing the human Ca$_v$2.2α (α1$_B$) subunit, along with the human β3 and α2δ1 auxiliary subunits were created following sequential transfection and selection of human embryonic kidney (HEK293) cells. HEK293 cells were cultured in Dulbecco's modified Eagles media/F12 media (Invitrogen, Cat #041-95750V) containing 10% fetal bovine serum, with added L-glutamine (2 mM; Invitrogen, Cat #25030-024) and non-essential amino acids (5%; Invitrogen, Cat #11140-035). Initially HEK293 cells were transfected with two plasmid vectors for expression of the hCa$_v$2.2 α subunit (pCIN5-hCa$_v$2.2 which carries a neomycin resistance marker) and the hCa$_v$ β3 subunit (pCIH-hCa$_v$ β3 which carries a hygromycin resistance marker). Clonal cell lines were isolated following selection in media supplemented with 0.4 mg ml$^{-1}$ Geneticin G418 (Invitrogen, Cat #10131-027) and 0.1 mg ml$^{-1}$ hygromycin (Invitrogen, Cat #10687-010). These clonal cell lines were assessed for Ca$_v$2.2 α/β3-mediated current expression using the IonWorks planar array electrophysiology technology (described below). A clonal line was identified that gave a reasonable level of functional Ca$_v$2.2 α/β3 current expression. This cell line was transfected with a plasmid vector for expression of the human α2δ1 subunit (pCIP-α2δ1 which carries a puromycin resistance marker) and clonal cell lines isolated following selection in media containing 0.62 μg ml$^{-1}$ puromycin (Sigma, Cat # P-7255), in addition to 0.4 mg ml$^{-1}$ Geneticin G418 and 0.1 mg ml$^{-1}$ hygromycin. Several cell lines were identified that gave robust levels of Ca$_v$2.2 α/β3/α2δ1-mediated current expression and one of these was selected for compound profiling. Expression of all three subunits within this cell line was continuously maintained by the inclusion of G418 (0.4 mg ml$^{-1}$), hygromycin (0.1 mg ml$^{-1}$) and puromycin (0.62 μg ml$^{-1}$). Cells were maintained at 37° C. in a humidified environment containing 5% $CO_2$ in air. Cells were liberated from the T175 culture flasks for passage and harvesting using TrpLE (Invitrogen, Cat #12604-013).

Cell Preparation

Cells were grown to 30-60% confluence in T175 flasks and maintained at 30° C. for 24 hrs prior to recording. Cells were lifted by removing the growth media, washing with $Ca^{2+}$ free PBS (Invitrogen, Cat #14190-094) and incubating with 3 ml of warmed (37° C.) TrpLE (Invitrogen, Cat #12604-013) for 6 minutes. Lifted cells were suspended in 10 ml of extracellular buffer. Cell suspension was then placed into a 15 ml tube and centrifuged for 2 minutes at 700 rpm. After centrifugation, the supernatant was removed and the cell pellet was resuspended in 4.5 ml of extracellular solution.

Electrophysiology

Currents were recorded at room temperature (21-23° C.) using the IonWorks planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential ($V_H$) of −90 mV to +10 mV were applied for 20 ms and repeated 10 times at a frequency of 10 Hz. In all experiments, the test pulse protocol was performed in the absence (preread) and presence (post-read) of a compound. Pre- and post-reads were separated by a compound addition followed by a 3-3.5 min incubation.

Solutions and Drugs

The intracellular solution contained the following (in mM): K-gluconate 120, KCl 20 mM, $MgCl_2$ 5, EGTA 5, HEPES 10, adjusted to pH 7.3. Amphotericin was prepared as 30 mg/ml stock solution and diluted to a final working concentration of 0.2 mg ml$^{-1}$ in intracellular buffer solution. The extracellular solution contained the following (in mM): Na-gluconate 120, NaCl 20, $MgCl_2$ 1, HEPES 10, $BaCl_2$ 5, adjusted to pH 7.4.

Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using seal resistance (>40 MΩ), resistance reduction (>35%) and peak current amplitude (>200 pA) in the absence of compound to eliminate unsuitable cells from further analysis. Paired comparisons between pre-compound and post-compound additions were used to determine the inhibitory effect of each compound. The concentrations of compounds required to inhibit current elicited by the 1$^{st}$ depolarising pulse by 50% (tonic pIC50) were determined by fitting of the Hill equation to the concentration response data. In addition the use-dependent inhibitory properties of the compounds were determined by assessing the effect of compounds on the 10$^{th}$ versus 1$^{st}$ depolarising pulse. The ratio of the 10$^{th}$ over 1$^{st}$ pulse was determined in the absence and presence of drug and the % use-dependent inhibition calculated. The data was fitted using the same equation as for the tonic $pIC_{50}$ and the concentration producing 30% inhibition (use-dependent $pUD_{30}$) determined.

Assay 2 (T-Type):

The ability of the compounds of the invention to modulate the voltage-gated calcium channel subtype Cav3.2 (T-Type) may be determined by the following assay.

Cell Biology

Stable cell lines expressing hCav3.2 channels were created by transfecting HEK293 cells with the plasmid pCIN5-human-alpha1H. pCIN5-human-alpha1H predicted protein is equivalent to the full-length human variant NP_066921 for the human ion channel CACNA1H (voltage dependent calcium channel T type alpha 1H subunit), the longer variant form. It contains minor alleles for two SNPs (Ala 664 and Arg 2077). However, in the absence of any knowledge about compound binding at this ion channel, these rare variants are not seen as issues. Stable cell line was selected by 500 ug/ml G418 (geneticin). The best cell line clone was selected by IonWorks. Cells were cultured in DMEM/F12 medium supplemented by 10% Foetal Bovine Serum (Gibco/Invitrogen #041-95750), 1% non-essential amino acids (PAA, M11-003) and 1% Penicillin-Streptomycin (Invitrogen, 15140-122). 500 ug/ml of G418 (PAA, P11-012) was added to maintain channel expression. Cells were grown and maintained at 37° C. in a humidified environment containing 5% CO2 in air. Cells were detached from the T175 culture flask for passage and harvesting using TrypLE (Gibco/Invitrogen cat #12604). For the experiment, cells were plated in a T175 culture flask 48 hours before running the assay to reach a 50-80% confluence the day of the experiment.

Cell Preparation

Cells were grown to 50-80% confluence in a T175 flask. Cells were removed from the incubator and the media was aspirated. Cells were washed with 5 ml of warmed (37° C.) TrypLE and then 3 ml of warmed (37° C.) TrypLE was added to the flask for 6 min. The flask was tapped to dislodge cells and 5 ml of warmed (37° C.) external buffer with barium and magnesium was added to prepare a cell suspension. Cell suspension was then placed into a 15 ml centrifuge tube and centrifuged for 2 min at 1000 rpm. After centrifugation, the supernatant was removed and the cell pellet was resuspended in 4-5 ml of pre-warmed (37° C.) external solution with barium and magnesium using a 5 ml pipette to break up the pellet.

Electrophysiology

Currents were recorded at room temperature using the IonWorks Quattro™ planar array electrophysiology technology (Molecular Devices Corp.) with PatchPlate™ PPC for Ionworks Quattro (Molecular Devices, 9000-0902). Stimulation protocols and data acquisition were carried out using a microcomputer (Dell Pentium 4). In order to determine planar electrode hole resistances (Rp), a 10 mV voltage step was applied across each well. These measurements were performed before cell addition. After cell addition a seal test was performed by applying a voltage step from −80 mV to −70 mV for 160 ms prior to antibiotic amphotericin-B solution (Sigma, P11-012) circulation to achieve intracellular access. Leak subtraction was conducted in all experiments by applying a 80 ms hyperpolarizing (10 mV) prepulse followed by a 80 ms at the holding potential before the test pulses, to measure leak current. Test pulses stepping from the holding potential of −120 mV to −40 mV were applied for 25 ms and repeated 10 times at a frequency of 3 Hz. In all experiments, the test pulse protocol was performed in the absence (pre-read) and presence (post-read) of a compound. Pre- and post-reads were separated by a compound addition followed by a 10 minute incubation.

Solutions and Drugs

The intracellular solution contained the following (in mM): K-gluconate 120, KCl 20, MgCl2 5, EGTA 5, HEPES 10, adjusted to pH 7.35.

Amphotericin-B solution was prepared as 50 mg/ml stock solution in DMSO and diluted to a final working concentration of 0.2 mg/ml in intracellular solution. The external solution contained the following (in mM): Na-gluconate 120, NaCl 20, HEPES 10, MgCl2 1, BaCl2 5, with a pH of 7.35.

Compounds were prepared in DMSO as 10 mM stock solutions and subsequent 1:3 serial dilutions were performed. Finally the compounds were diluted 1:100 in external solution containing 0.05% pluronic acid.

Data Analysis

The recordings were analysed and filtered using seal resistance (>20 MΩ), peak current amplitude (>100 pA) and pre-compound seal resistance (>40 MΩ) in the absence of compound to eliminate unsuitable cells from further analysis. Paired comparisons between pre-drug and post-drug additions were used to determine the inhibitory effect of each compound. Data were normalised to the high control (1% DMSO) and low control (500 uM Nickel Chloride from Sigma-Aldrich, N6136). The normalised data were analysed by using ActivityBase software. The concentrations of compounds required to inhibit current elicited by the $1^{st}$ depolarising pulse by 50% (tonic pIC50) were determined by fitting of the four parameter logistic function to the concentration response data. In addition the use-dependent inhibitory properties of the compounds were determined by assessing the effect of compounds on the $10^{th}$ versus $1^{st}$ depolarising pulse. The ratio of the $10^{th}$ over $1^{st}$ pulse was calculated in the absence and presence of drug and the % use-dependent inhibition calculated. The data was fitted using the same equation as for the tonic $pIC_{50}$ and the concentration producing 30% inhibition (use-dependent $pUD_{30}$) calculated.

Compounds 1 to 15 and 20 to 29 were tested in assay 1. Compounds 1 to 4, 7, 9 to 11, 13, 15, 20 and 26 were tested in assay 2. Compounds were tested in the form as described herein. All compounds tested have been tested one or more times (up to 6 times). Variations in $pUD_{30}$ and $pIC_{50}$ values may arise between tests.

Activity of Compounds in Assay 1 (N-Type):

The compounds 1 to 15 and 20 to 31 exhibited a $pUD_{30}$ value of 4.5 or more than 4.5. The compounds 1 to 13, 15, 20 to 26 and 28 to 31 exhibited a $pUD_{30}$ value of 5.0 or more than 5.0. The compounds 1 to 4, 7 to 11, 13, 15, 20 to 26, 30 and 31 exhibited a $pUD_{30}$ value of 5.5 or more than 5.5. Compound 3 exhibited a $pUD_{30}$ of 5.8.

The compounds 1 to 3, 6, 8 to 10, 13 to 15, 20, 25, 27, 29 and 30 exhibited a $pIC_{50}$ value of 4.5 or more than 4.5. The compounds 1, 2, 10 and 13 exhibited a $pIC_{50}$ value of 5.0 or more than 5.0. No compound exhibited a $pIC_{50}$ value of 5.5 or more than 5.5. Compound 3 exhibited a $pIC_{50}$ of 4.6.

Activity of Compounds in Assay 2 (T-Type):

The compounds 1 to 4, 7, 9 to 11, 13, 15, 20, 26, 30 and 31 exhibited a $pUD_{30}$ value of 4.5 or more than 4.5. The compounds 1 to 4, 7, 9 to 11, 13, 15, 20, 26, 30 and 31 exhibited a $pUD_{30}$ value of 5.0 or more than 5.0. The compounds 4, 7 to 10, 13, 15 and 30 exhibited a $pUD_{30}$ value of 5.5 or more than 5.5. Compound 3 exhibited a $pUD_{30}$ of 5.4.

The compounds 1 to 3, 7, 9, 10, 15, 26 and 30 exhibited a $pIC_{50}$ value of 4.5 or more than 4.5. No compound exhibited a $pIC_{50}$ value of 5.0 or more than 5.0. No compound exhibited a $pIC_{50}$ value of 5.5 or more than 5.5. Compound 3 exhibited a $pIC_{50}$ of 4.6.

The invention claimed is:
1. A compound of formula (I), or a salt thereof:

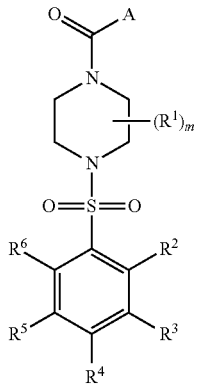

wherein A is selected from
(a) 2-quinolinyl,
(b) 5-quinolinyl,
(c) 7-quinolinyl,
(d) 8-quinolinyl, and
(e) isoquinolinyl;
and wherein A is unsubstituted or substituted with 1 to 3 substituents independently selected from $C_{1-4}$ alkyl;
m is 0, 1 or 2;
where present, each $R^1$ is $C_{1-4}$ alkyl;
$R^2$ is H, halogen, $C_{1-4}$ alkyl, $C_{1-4}$ alkoxy, cyano, $C_{1-4}$ haloalkyl or $C_{1-4}$ haloalkoxy;
$R^3$ is H, halogen, $C_{1-4}$ alkyl, $C_{1-4}$ alkoxy, cyano, $C_{1-4}$ haloalkyl or $C_{1-4}$ haloalkoxy;
$R^4$ is H, halogen, $C_{1-4}$ alkyl, $C_{1-4}$ alkoxy, cyano, $C_{1-4}$ haloalkyl or $C_{1-4}$ haloalkoxy;
$R^5$ is H, halogen, $C_{1-4}$ alkyl, $C_{1-4}$ alkoxy, cyano, $C_{1-4}$ haloalkyl or $C_{1-4}$ haloalkoxy;
$R^6$ is H, halogen, $C_{1-4}$ alkyl, $C_{1-4}$ alkoxy, cyano, $C_{1-4}$ haloalkyl or $C_{1-4}$ haloalkoxy;
such that at least 1 of $R^2$, $R^3$, $R^4$, $R^5$ and $R^6$ is a group other than H;
with the proviso that the compound is not
8-({4-[(3-bromophenyl)sulfonyl]-1-piperazinyl}carbonyl)quinoline,
8-({4-[(4-fluorophenyl)sulfonyl]-1-piperazinyl}carbonyl)quinoline,
8-{[4-({4-[(trifluoromethyl)oxy]phenyl}sulfonyl)-1-piperazinyl]carbonyl}quinoline,
8-[(4-{[4-(trifluoromethyl)phenyl]sulfonyl}-1-piperazinyl)carbonyl]quinoline,
2-{[4-({4-[(trifluoromethyl)oxy]phenyl}sulfonyl)-1-piperazinyl]carbonyl}quinoline,
8-({4-[(4-bromophenyl)sulfonyl]-1-piperazinyl}carbonyl)quinoline,
2-({4-[(4-bromophenyl)sulfonyl]-1-piperazinyl}carbonyl)quinoline,
8-[(4-{[4-chloro-3-(trifluoromethyl)phenyl]sulfonyl}-1-piperazinyl)carbonyl]quinoline,
4-{[4-(8-quinolinylcarbonyl)-1-piperazinyl]sulfonyl}benzonitrile,
2-[(4-{[4-(trifluoromethyl)phenyl]sulfonyl}-1-piperazinyl)carbonyl]quinoline,
2-[(4-{[3-(trifluoromethyl)phenyl]sulfonyl}-1-piperazinyl)carbonyl]quinoline,
2-({4-[(3-chlorophenyl)sulfonyl]-1-piperazinyl}carbonyl)quinoline,
2-({4-[(4-fluorophenyl)sulfonyl]-1-piperazinyl}carbonyl)quinoline,
2-({4-[(3-fluorophenyl)sulfonyl]-1-piperazinyl}carbonyl)quinoline,
[4-[(3,4-dichlorophenyl)sulfonyl]-1-piperazinyl]-2-quinolinyl-methanone,
[4-[(2,5-dichlorophenyl)sulfonyl]-1-piperazinyl]-2-quinolinyl-methanone,
[4-[[4-(1-methylpropyl)phenyl]sulfonyl]-1-piperazinyl]-2-quinolinyl-methanone,
2-[[4-(2-quinolinylcarbonyl)-1-piperazinyl]sulfonyl]benzonitrile,
[4-[[2-chloro-5-(trifluoromethyl)phenyl]sulfonyl]-1-piperazinyl]-2-quinolinyl-methanone,
[4-[(2,6-difluorophenyl)sulfonyl]-1-piperazinyl]-5-quinolinyl-methanone,
[4-[(3,4-dimethoxyphenyl)sulfonyl]-1-piperazinyl]-2-quinolinyl-methanone,
[4-[(2-chlorophenyl)sulfonyl]-1-piperazinyl]-2-quinolinyl-methanone,
[4-[[4-(1,1-dimethylethyl)phenyl]sulfonyl]-1-piperazinyl]-2-quinolinyl-methanone,
[4-[(2,6-dichlorophenyl)sulfonyl]-1-piperazinyl]-2-quinolinyl-methanone,
[4-[(3,4-difluorophenyl)sulfonyl]-1-piperazinyl]-2-quinolinyl-methanone,
[4-[(3,4-dimethylphenyl)sulfonyl]-1-piperazinyl]-2-quinolinyl-methanone,
[4-[(2,3,4,5,6-pentamethylphenyl)sulfonyl]-1-piperazinyl]-8-quinolinyl-methanone,
8-quinolinyl[4-[(2,4,6-trimethylphenyl)sulfonyl]-1-piperazinyl]-methanone,
[4-[[4-chloro-3-(trifluoromethyl)phenyl]sulfonyl]-1-piperazinyl]-2-quinolinyl-methanone,
[4-[(4-bromo-2-chlorophenyl)sulfonyl]-1-piperazinyl]-2-quinolinyl-methanone,
[4-[(2,5-dimethylphenyl)sulfonyl]-1-piperazinyl]-2-quinolinyl-methanone,
[4-[(3,4-diethoxyphenyl)sulfonyl]-1-piperazinyl]-8-quinolinyl-methanone,
[4-[(4-methylphenyl)sulfonyl]-1-piperazinyl]-8-quinolinyl-methanone,
[4-[(4-methylphenyl)sulfonyl]-1-piperazinyl]-2-quinolinyl-methanone,
[4-[(2,4-dimethylphenyl)sulfonyl]-1-piperazinyl]-2-quinolinyl-methanone,
[4-[(4-ethoxyphenyl)sulfonyl]-1-piperazinyl]-2-quinolinyl-methanone,
[4-[(4-methoxyphenyl)sulfonyl]-1-piperazinyl]-2-quinolinyl-methanone,
[4-[(2,3-dichlorophenyl)sulfonyl]-1-piperazinyl]-2-quinolinyl-methanone,
2-quinolinyl[4-[(2,3,5,6-tetramethylphenyl)sulfonyl]-1-piperazinyl]-methanone,
[4-[(2-fluorophenyl)sulfonyl]-1-piperazinyl]-2-quinolinyl-methanone,
2-quinolinyl[4-[[2-(trifluoromethyl)phenyl]sulfonyl]-1-piperazinyl]-methanone, or
[4-[(4-chlorophenyl)sulfonyl]-1-piperazinyl]-2-quinolinyl-methanone.

2. The compound or salt according to claim 1, wherein A is unsubstituted or substituted with methyl.

3. The compound or salt according to claim 1 or 2, wherein m is 0 or 1.

4. The compound or salt according to claim 1, wherein $R^1$ is methyl.

5. The compound or salt according to claim 1, wherein $R^2$ is selected from H or methyl.

6. The compound or salt according to claim 1, wherein $R^3$ is H.

7. The compound or salt according to claim 1, wherein $R^4$ is selected from cyano, $C_{1-4}$ haloalkyl or $C_{1-4}$ haloalkoxy.

8. The compound or salt according to claim 1, wherein $R^5$ is H.

9. The compound or salt according to claim 1, wherein a compound or a salt is selected from 7-[((2S)-2-Methyl-4-{[4-(trifluoromethyl)phenyl]sulfonyl}-1-piperazinyl)carbonyl]quinoline
   8-Methyl-7-{[4-{{4-[(trifluoromethyl)oxy]phenyl}sulfonyl)-1-piperazinyl]carbonyl}quinoline
   2-[(4-{4-(Trifluoromethyl)phenyl]sulfonyl}-1-piperazinyl)carbonyl]quinoline
   7-[(4-{[4-(Trifluoromethyl)phenyl]sulfonyl}-1-piperazinyl)carbonyl]quinoline
   5-[(4-{[4-(Trifluoromethyl)phenyl]sulfonyl}-1-piperazinyl)carbonyl]quinoline
   4-{[(3S)-3-Methyl-4-(7-quinolinylcarbonyl)-1-piperazinyl]sulfonyl}benzonitrile
   3-Methyl-4-{[4-(7-quinolinylcarbonyl)-1-piperazinyl]sulfonyl}benzonitrile
   3-Methyl-4-{[(3S)-3-methyl-4-(7-quinolinylcarbonyl)-1-piperazinyl]sulfonyl}benzonitrile
   3-Methyl-4-({4-((2-methyl-7-quinolinyl)carbonyl}-1-piperazinyl}sulfonyl)benzonitrile
   3-Methyl-4-({(3S)-3-methyl-4-[(2-methyl-7-quinolinyl)carbonyl]-1-piperazinyl}sulfonyl)benzonitrile
   3-Methyl-4-{[(3S)-3-methyl-4-(8-quinolinylcarbonyl)-1-piperazinyl]sulfonyl}benzonitrile
   3-Methyl-4-{[(3S)-3-methyl-4-(5-quinolinylcarbonyl)-1-piperazinyl]sulfonyl}benzonitrile
   8-Methyl-7-[(4-{[4-(trifluoromethyl)phenyl]sulfonylr1-piperazinyl)carbonyl]quinoline
   4-{{(3S)-3-Methyl-4-[(8-methyl-7-quinolinyl)carbonyl)-1-piperazinyl}sulfonyl)benzonitrile
   3-Methyl-4-({(3S)-3-methyl-4-[(8-methyl-7-quinolinyl)carbonyl]-1-piperazinyl}sulfonyl)benzonitrile
   7-{[4-({4-[(Trifluoromethyl)oxy]phenyl}sulfonyl)-1-piperazinyl]carbonyl}quinoline
   7-{[(2S)-2-Methyl-4-({4-[(trifluoromethyl)oxy]phenyl}sulfonyl)-1-piperazinyl]carbonyl}quinoline
   7-{[(2S)-4-({4-[(Difluoromethyl)oxy]phenyl}sulfonyl)-2-methyl-1-piperazinyl]carbonyl}quinoline
   7-{[(2S)-4-({4-[(Difluoromethyl)oxy]phenyl}sulfonyl)-2-methyl-1-piperazinyl]carbonyl}-8-methylquinoline
   8-[((2S)-2-Methyl-4-{[4-(trifluoromethyl)phenyl]sulfonyl}-1-piperazinyl)carbonyl]isoquinoline
   1-[(4-{[4-(Trifluoromethyl)phenyl]sulfonyl}-1-piperazinyl)carbonyl]isoquinoline
   5-[(4-{[4-(Trifluoromethyl)phenyl]sulfonyl}-1-piperazinyl)carbonyl]isoquinoline
   3-[(4-{[4-(Trifluoromethyl)phenyl]sulfonyl}-1-piperazinyl)carbonyl]isoquinoline
   8-[(4-{[4-(Trifluoromethyl)phenyl]sulfonyl}-1-piperazinyl)carbonyl]isoquinoline
   4-[(4-{[4-(Trifluoromethyl)phenyl]sulfonyl}-1-piperazinyl)carbonyl]isoquinoline
   4-{[4-(8-Isoquinolinylcarbonyl)-1-piperazinyl]sulfonyl}-3-methylbenzonitrile
   4-{[(3S)-4-(8-Isoquinolinylcarbonyl)-3-methyl-1-piperazinyl]sulfonyl}benzonitrile
   4-{[(3S)-4-(6-Isoquinolinylcarbonyl)-3-methyl-1-piperazinyl]sulfonyl}benzonitrile
   4-{[(3S)-4-(8-Isoquinolinylcarbonyl}-3-methyl-1-piperazinyl]sulfonyl}-3 methylbenzonitrile
   8-{[4-({4-[{Trifluoromethyl)oxy]phenyl}sulfonyl}-1-piperazinyl]carbonyl}quinolone
   8-[(4-{[4-(Trifluoromethyl)phenyl]sulfonyl}-1-piperazinyl)carbonyl)quinolone
   8-{[(2S)-4-({4-[(Difluoromethyl)oxy]phenyl}sulfonyl)-2-methyl-1-piperazinyl]carbonyl}quinoline
   3,5-Dimethyl-4-{[(3S)-3-methyl-4-(8-quinolinylcarbonyl)-1-piperazinyl]sulfonyl}benzonitrile
   3,5-Dimethyl-4-{[(3S)-3-methyl-4-(7-quinolinylcarbonyl)-1-piperazinyl]sulfonyl}benzonitrile
   7-{[4-({4-[(Difluoromethyl)oxy]phenyl}sulfonyl)-1-piperazinyl]carbonyl}-8-methylquinoline
   1-Methyl-8-{[4-({4-[(trifluoromethyl)oxy]phenyl}sulfonyl)-1-piperazinyl]carbonyl}isoquinoline
   3-Methyl-4-({4-[(1-methyl-8-isoquinolinyl)carbonyl]-1-piperazinyl}sulfonyl)benzonitrile
   3,5-Dimethyl-4-({4-[(1-methyl-8-isoquinolinyl)carbonyl]-1-piperazinyl}sulfonyl)benzonitrile
   3,5-Dimethyl-4-({(3S)-3-methyl-4-[(1-methyl-8-isoquinolinyl)carbonyl]-1-piperazinyl}sulfonyl)benzonitrile
   3-Methyl-4-({(3S)-3-methyl-4-[(1-methyl-8-isoquinolinyl)carbonyl]-1-piperazinyl}sulfonyl)benzonitrile
   8-{[(2S)-4-({4-[(Difluoromethyl)oxy]phenyl}sulfonyl)-2-methyl-1-piperazinyl]carbonyl}-1-methylisoquinoline
   8-{[4-({4-[(Difluoromethyl)oxy]phenyl}sulfonyl)-1-piperazinyl]carbonyl}-1-methylisoquinoline
   8-{[(2S)-4-({4-[(Fluoromethyl)oxy]phenyl}sulfonyl)-2-methyl-1-piperazinyl]carbonyl}quinoline
   8-{[(2S)-4-({4-[(Fluoromethyl)oxy]-2-methylphenyl}sulfonyl)-2-methyl-1-piperazinyl]carbonyl}quinoline
   7-{[(2S)-4-({4-[(Fluoromethyl)oxy]-2-methylphenyl}sulfonyl)-2-methyl-1-piperazinyl]carbonyl}quinoline
   7-{[2S)-4-({4-[(Fluoromethyl)oxy)phenyl}sulfonyl)-2-methyl-1-piperazinyl]carbonyl}quinoline
   8-{[(2S)-4-({4-[(Fluoromethyl)oxy]phenyl}sulfonyl)-2-methyl-1-piperazinyl]carbonyl}-1-methylisoquinoline
   or a salt thereof.

10. The compound or salt according to claim 1, wherein the salt is pharmaceutically acceptable.

11. A method for the treatment of neuropathic pain, inflammatory pain, or migraine pain in a human or other mammal in need thereof comprising administering to said human or mammal a therapeutically effective amount of a compound or pharmaceutically acceptable salt according to claim 10.

12. A pharmaceutical composition comprising (a) a compound or pharmaceutically acceptable salt according to claim 10 and (b) a pharmaceutically acceptable excipient.

* * * * *